US005525713A

United States Patent [19]

Raikhel

[11] Patent Number: 5,525,713

[45] Date of Patent: *Jun. 11, 1996

[54] DNA ENCODING POLYPEPTIDES ENABLING SORTING OF PROTEINS TO VACUOLES IN PLANTS

[75] Inventor: Natasha V. Raikhel, Okemos, Mich.

[73] Assignee: Board of Trustees operating Michigan State University, East Lansing, Mich.

[ * ] Notice: The term of this patent shall not extend beyond the expiration date of Pat. No. 5,360,726.

[21] Appl. No.: 173,515

[22] Filed: Dec. 23, 1993

Related U.S. Application Data

[63] Continuation-in-part of Ser. No. 917,665, Jul. 20, 1992, Pat. No. 5,276,269, which is a continuation-in-part of Ser. No. 406,318, Sep. 12, 1989, abandoned, and a continuation-in-part of Ser. No. 791,930, Nov. 12, 1991, Pat. No. 5,360,726, which is a continuation-in-part of Ser. No. 612,200, Nov. 13, 1990, abandoned, which is a continuation-in-part of Ser. No. 406,318, Sep. 12, 1989, abandoned.

[51] Int. Cl.[6] ........................... C12N 15/62; C12N 15/29

[52] U.S. Cl. .......................... 536/23.4; 536/23.6; 935/48

[58] Field of Search ................................ 536/23.4, 23.6; 935/9, 11, 48, 49, 50; 435/320.1, 172.3

[56] References Cited

PUBLICATIONS

Blobel, G., & Dobberstein, D., J. Cell Biol. 67, 835–851 (1975).
Rothman, J. E., Cell 50, 521–522 (1987).
Wieland, F. T. et al., Cell 50, 289–300 (1987).
Dorel, C., et al., J. Cell Biol. 108, 327–337 (1989).
Denecke, J., et al., Plant Cell 2, 51–59 (1990).
Verner, K. et al., Protein translocation across memberanes 241, 1307–1313 (1988).
Kornfeld, S., et al., Ann. Rev. Cell Biol. 5, 483–525 (1989).
Gabel, C. A., et al., Proc. Natl. Acad. Sci. USA 80, 775–779 (1983).
Stevens, T. H. et al., Cell 30, 439–448 (1982).
Voelker, T. A., et al., Cell 1, 95–104 (1989).
Wilkins, T. A., et al., Plant Cell 2 301–313 (1990).
Sonnewald, U., et al., Plant Cell 2, 345–355 (1990).
Johnson, L. M. et al., Cell 28, 875–885 (1987).
Valls, L. A., et al., Cell 48, 887–897 (1987).
Valls, L. A., et al., J. Cell Biol. 111, 361–368 (1990).
Klionsky, D. J., et al., Mol. Cell Biol. 3, 2105–2116 (1988).
Tague, B. W., et al., J. Cell Biochem. Suppl. 13D, 230 (1989).
Tague, B. W., et al., Plant Cell 2, 533–546 (1990).
Chrispeels, M. J., Ann. Rev. Plant Physiol. Plant Molc. Biol. 42, 21–53 (1991).
Raikhel N. V., et al., Proc. Natl. Acad. Sci. 84, 6745–6749 (1987).
Smith et al., Plant Molecular Biology 13, 601–603 (1989).
Smith, et al., Plant Physiology 91, 473–476 (1989).
Wilkins, et al., 1 541–549 (1989).
Mansfield, M. A. et al., Planta 173, 482–489 (1988).
Kunkel, T. A., et al., Methods Enzymol. 154, 367–382 (1987).
Vieira, J., et al., Methods Enzymol. 153, 3–11 (1987).
An, G., et al., Plant Molec. Biol. Manual A3, 1 –19 (1988).
Murashige, T., et al., Physiol. Plant 15, 473–497 (1962).
Negrutiu, I., et al., Plant Mol. Biol. 8, 363–373 (1987).
Damm, B., et al., Mol. Gen. Genet. 217, 6–12 (1989).
An, G., Plant Physiol. 79, 568–570 (1985).
Nagy, F., et al., Plant Molecular Biology Manual B4, 1–29 (1988).
Feinberg, A. P., et al., Anal., Biochem. 132, 6–13 (1983).
Lerner, D. R., et al., Plant Physiol. 91, 124–129 (1989).
Raikhel, N. V., et al., Planta 126, 406–414 (1988).
Boller, T., et al., Plant Physiol. 63, 1123–1132 (1979).
Mishkind, M. L., et al., Science 220, 1290–1292 (1983).
Peumans, W. J., et al., Planta 154, 568–572 (1982).
Wright, C. S., J. Mol. Biol. 194, 501–529 (1987).
Shinshi, H. et al., Proc. Natl. Acad. Sci. USA 85, 5541–5545 (1988).
Deloose, M., et al., Gene 70, 13–23 (1988).
Klionsky, D. J., et al., Mol. Cell Biol. 8 2105–2116 (1988).
Van Den Bulcke, M., et al., Proc. Natl. Acad. Sci. USA 86 2673–2677 (1989).
Neale, A. D., et al., Plant Cell 2, 673–684 (1990).
Tartakoff, A. M., Cell 32, 1026–1028 (1983).
Chrispeels, M. J., Planta 158, 140–151 (1983).
Montreuil, J., Biol. Cell 51, 115–131 (1984).
Stevens, T. H., et al., J. Cell Biol. 102, 1551–1557 (1986).
Metraux, J. P., et al., Proc. Natl. Acad. Sci. USA 86, 896–900 (1989).
Shinshi, H., et al., Plant Mol. Biol. 14, 357–368 (1990).
Shinshi, H., et al., Proc. Natl. Acad. Sci. USA 84, 89–93 (1987).
Sanger, F., et al., Proc. Natl. Acad. Sci. US 56, 5463–5467 (1977).
Bednarek, S. Y., et al., Plant Cell 2 1145–1155 (1990).
Towbin, H., et al., Proc. Natl. Acad. Sci. US 76, 4350–4354 (1979).
Blake, M. S. , et al., Anal. Biochem. 136, 175–179 (1984).
Lord, J. M., Endoplasmic reticulum & ribosomes In Isolation of Membranes & organelles from plant cells, J. L. Hall & A. L. Moore eds (New York: Academic Press), pp. 119–134 (1983).
Simcox, P. D., et al., L. Plant Physiol. 59, 1128–1132 (1977).
Firestone, G. L., & S. D. Winguth, Methods Enzymol. 182, 688–700 (1990).
Herman, E. M., et al., Plant Mol. Biol. Manual B13, 1–24 (1990).
Wright C. S., et al., Biochemistry 23, 280–287 (1984).
Linthorst, J. H. M., et al., Mol. Plant Microbe. Interact. 3, 252–258 (1990).
Matsuoka, K., et al., Proc. Natl. Acad. Sci. U.S. 88, 834–838 (1991).
Saalbach, G., et al., Plant Cell 3, 695–708 (1991).

*Primary Examiner*—Mary E. Mosher
*Attorney, Agent, or Firm*—Ian C. McLeod

[57] ABSTRACT

A DNA encoding a polypeptide enabling sorting of proteins to vacuoles in plants, particularly tobacco is described. Without this sequence, the protein is not sorted to the vacuoles. The polypeptide is attached to the C-terminal region of the protein and is particularly useful for sorting of lectins to the vacuole which are insecticidal.

6 Claims, 16 Drawing Sheets

FIG. 4A
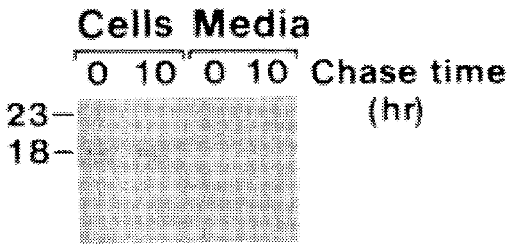
FIG. 4B
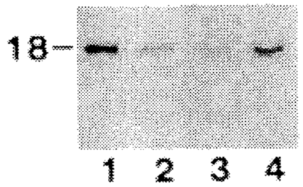
FIG. 5A
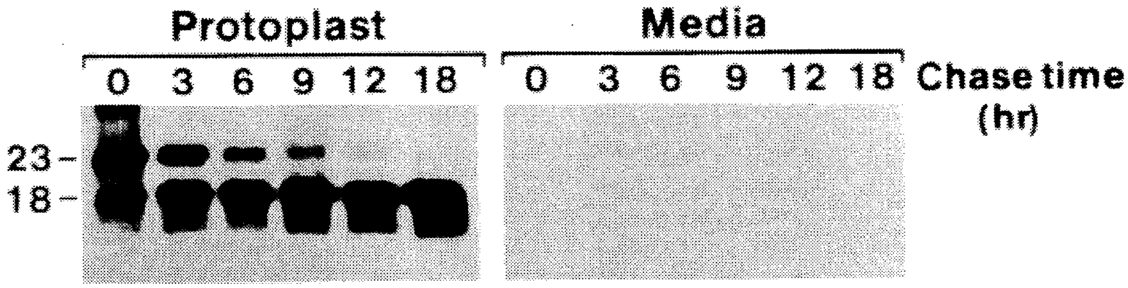
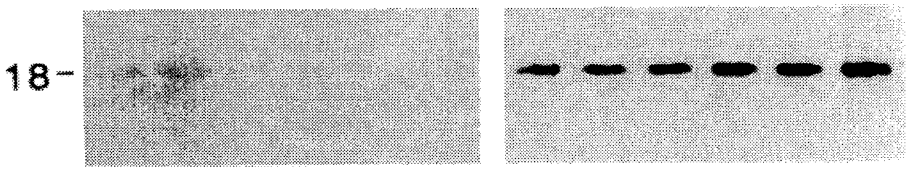
FIG. 5B

| | |
|---|---|
| BARLEY lectin | V F A E A I A A N* S T L V A E |
| WGA-A | V F A E A I T A N* S T L L Q E |
| WGA-B | V F A E A I A T N* S T L L A E |
| WGA-D | V F A G A I T A N* S T L L A E |
| RICE lectin | D G M A A I L A N N* G S V S F E G I I E S V A E L V |
| N. tabacum β-1,3-glucanase | V S G G V W D S S V E T N* A T A S L V S E M |
| N. plumbaginifolia β-1,3-glucanase | F S D R Y W D I S A E N N* A T A A S L I S E M |

FIG. 6

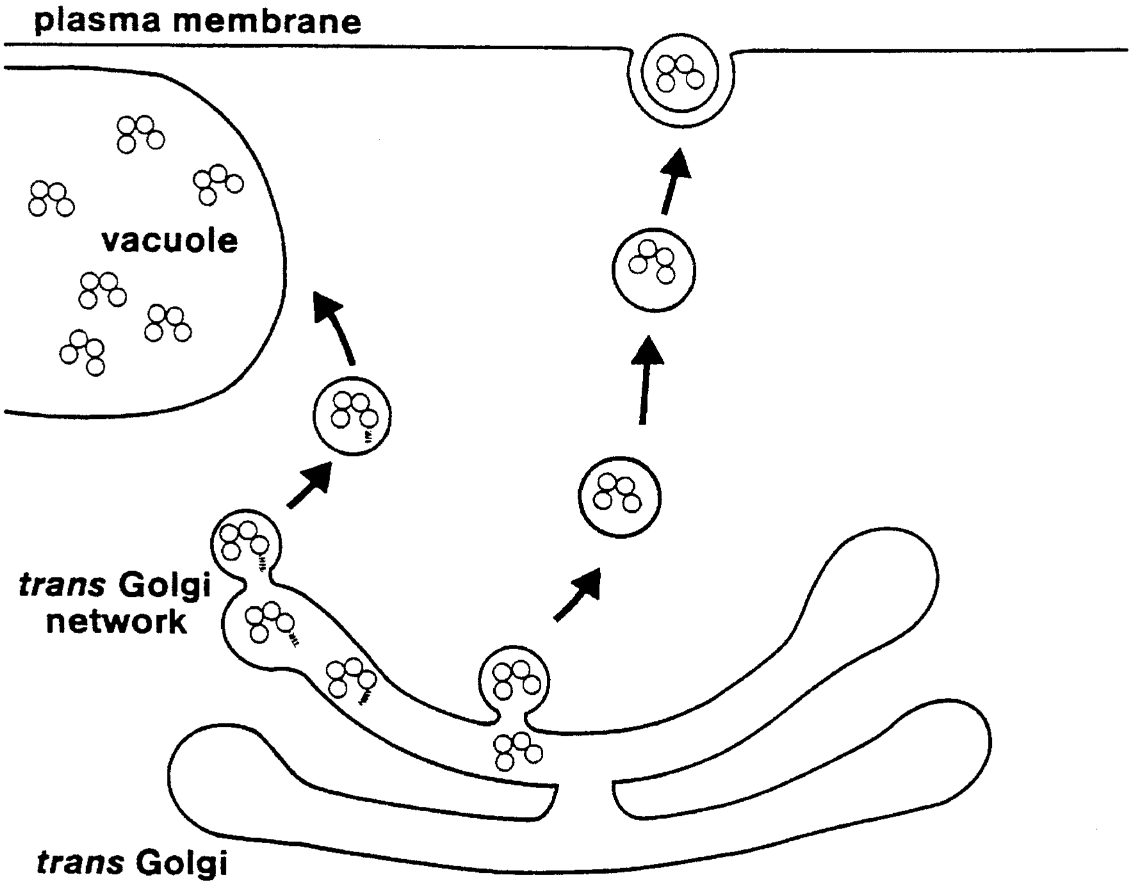
F I G. 7

FIG. 8A
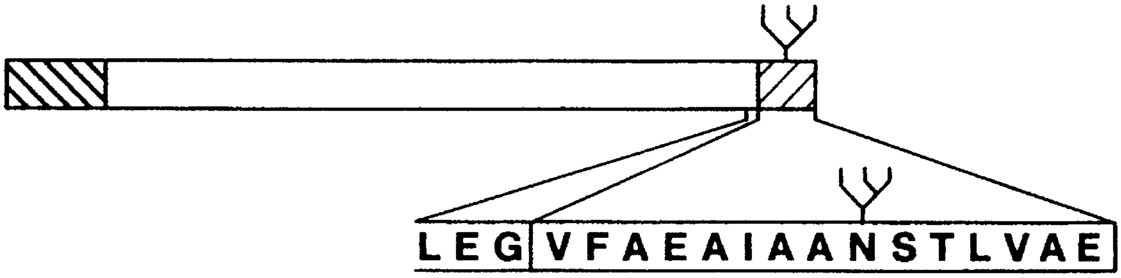
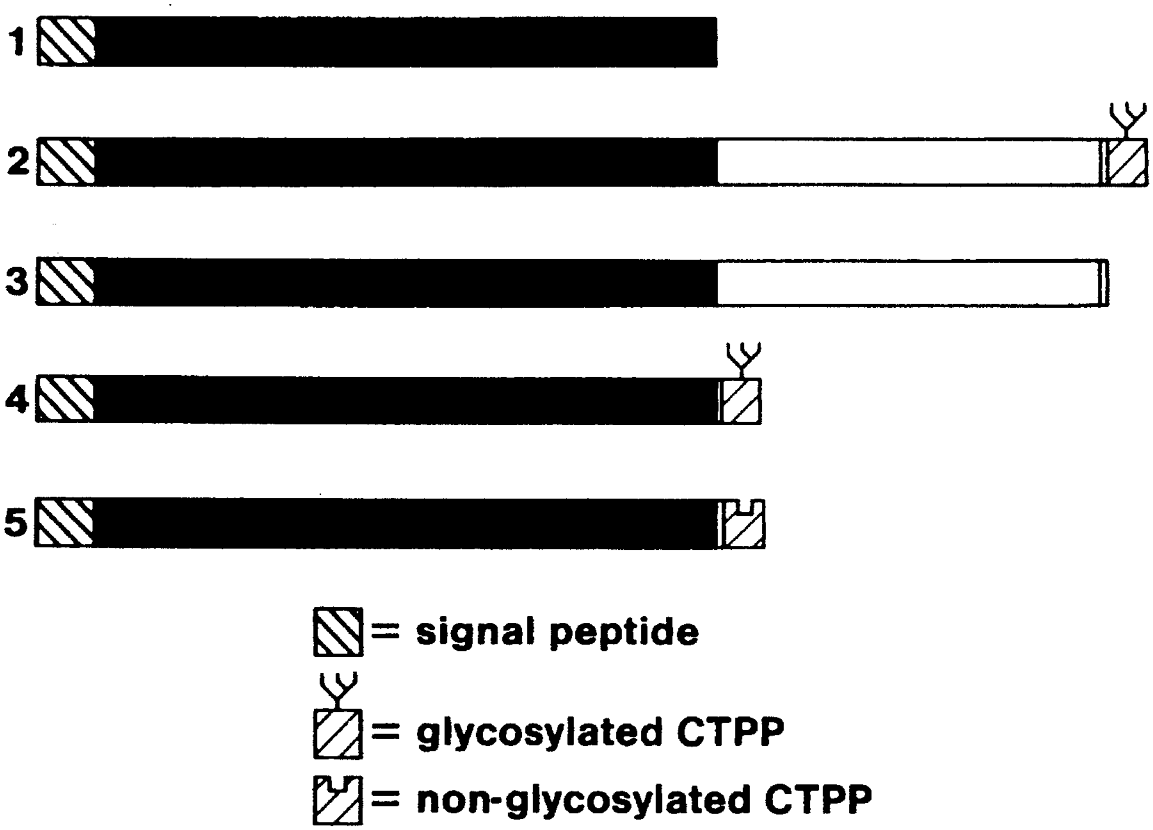
FIG. 8B

FIG. 12A
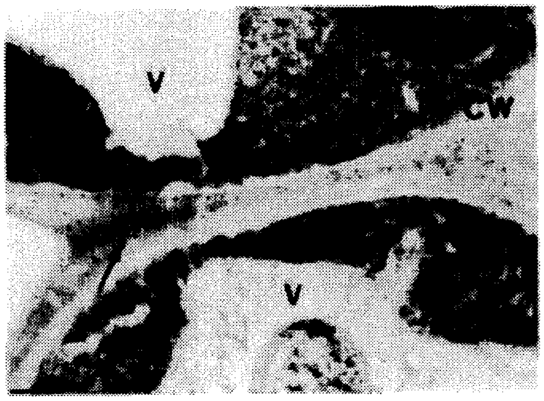
FIG. 12B
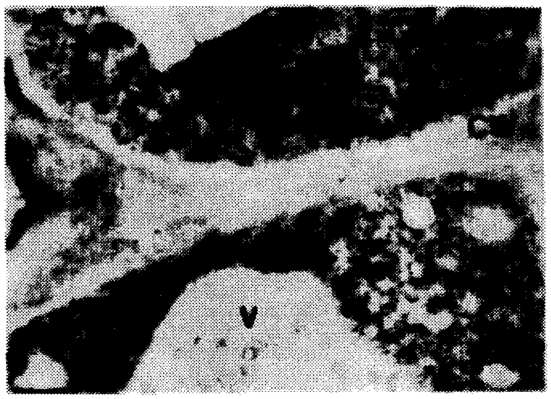
FIG. 12C
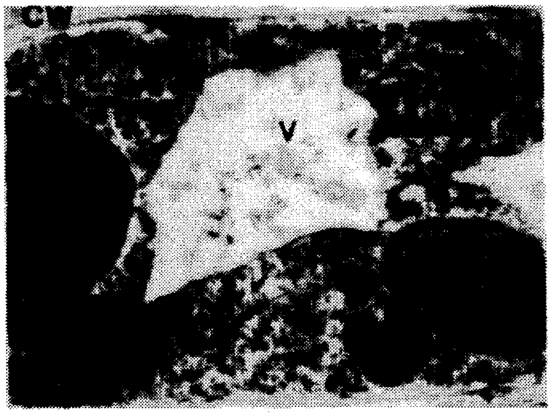
FIG. 12D

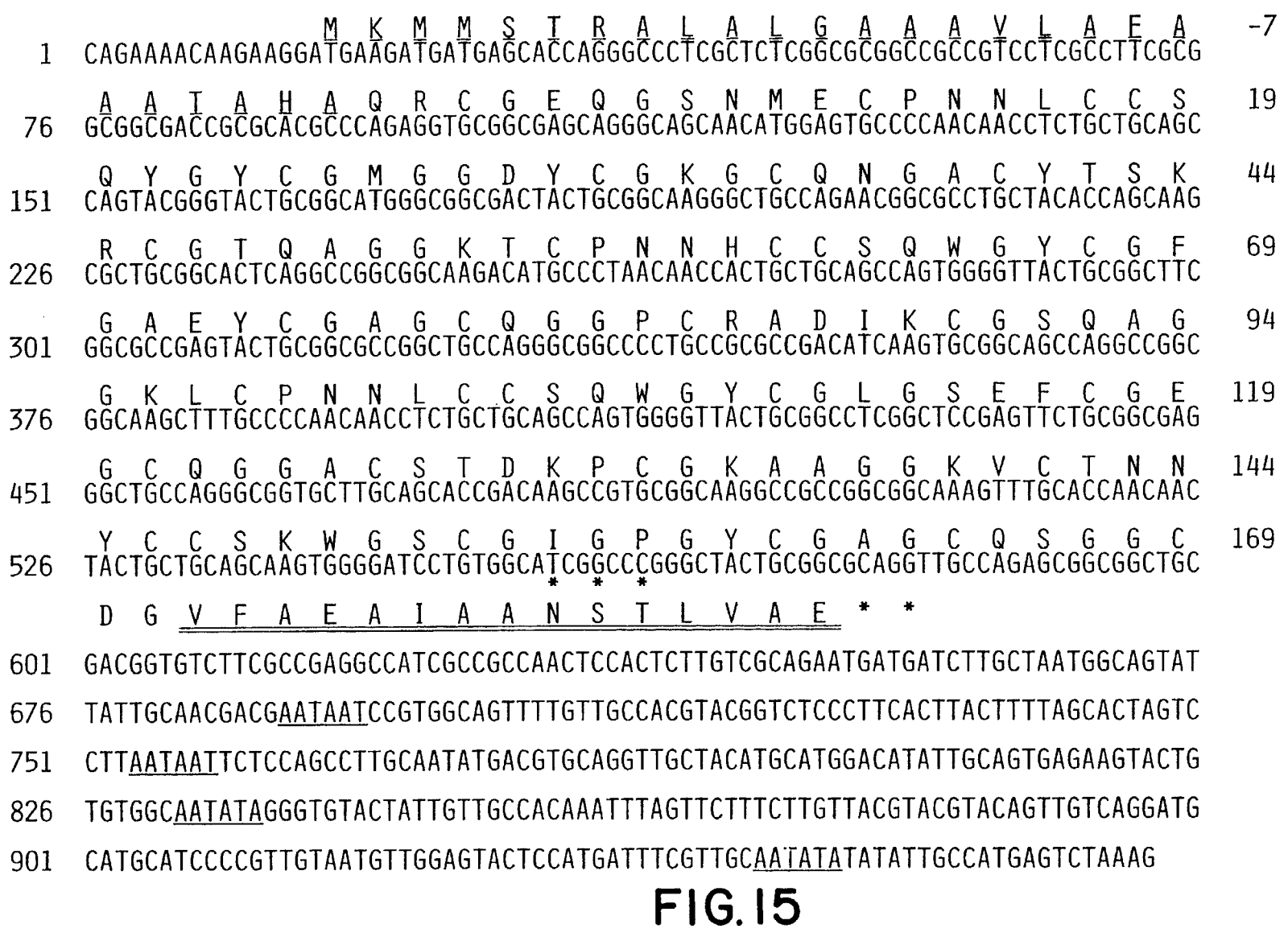

```
                     M  K  M  M  S  T  R  A  L  A  L  G  A  A  A  V  L  A  E  A    -7
  1 CAGAAAACAAGAAGGATGAAGATGATGAGCACCAGGGCCCTCGCTCTCGGCGCGGCCGCCGTCCTCGCCTTCGCG

     A  A  T  A  H  A  Q  R  C  G  E  Q  G  S  N  M  E  C  P  N  N  L  C  C  S    19
 76 GCGGCGACCGCGCACGCCCAGAGGTGCGGCGAGCAGGGCAGCAACATGGAGTGCCCCAACAACCTCTGCTGCAGC

     Q  Y  G  Y  C  G  M  G  G  D  Y  C  G  K  G  C  Q  N  G  A  C  Y  T  S  K    44
151 CAGTACGGGTACTGCGGCATGGGCGGCGACTACTGCGGCAAGGGCTGCCAGAACGGCGCCTGCTACACCAGCAAG

     R  C  G  T  Q  A  G  G  K  T  C  P  N  N  H  C  C  S  Q  W  G  Y  C  G  F    69
226 CGCTGCGGCACTCAGGCCGGCGGCAAGACATGCCCTAACAACCACTGCTGCAGCCAGTGGGGTTACTGCGGCTTC

     G  A  E  Y  C  G  A  G  C  Q  G  G  P  C  R  A  D  I  K  C  G  S  Q  A  G    94
301 GGCGCCGAGTACTGCGGCGCCGGCTGCCAGGGCGGCCCCTGCCGCGCCGACATCAAGTGCGGCAGCCAGGCCGGC

     G  K  L  C  P  N  N  L  C  C  S  Q  W  G  Y  C  G  L  G  S  E  F  C  G  E   119
376 GGCAAGCTTTGCCCCAACAACCTCTGCTGCAGCCAGTGGGGTTACTGCGGCCTCGGCTCCGAGTTCTGCGGCGAG

     G  C  Q  G  G  A  C  S  T  D  K  P  C  G  K  A  A  G  G  K  V  C  T  N  N   144
451 GGCTGCCAGGGCGGTGCTTGCAGCACCGACAAGCCGTGCGGCAAGGCCGCCGGCGGCAAAGTTTGCACCAACAAC

     Y  C  C  S  K  W  G  S  C  G  I  G  P  G  Y  C  G  A  G  C  Q  S  G  G  C   169
526 TACTGCTGCAGCAAGTGGGGATCCTGTGGCATCGGCCCGGGCTACTGCGGCGCAGGTTGCCAGAGCGGCGGCTGC
                                      *  *  *

     D  G  V  F  A  E  A  I  A  A  N  S  T  L  V  A  E  *  *

601 GACGGTGTCTTCGCCGAGGCCATCGCCGCCAACTCCACTCTTGTCGCAGAATGATGATCTTGCTAATGGCAGTAT

676 TATTGCAACGACGAATAATCCGTGGCAGTTTTGTTGCCACGTACGGTCTCCCTTCACTTACTTTTAGCACTAGTC

751 CTTAATAATTCTCCAGCCTTGCAATATGACGTGCAGGTTGCTACATGCATGGACATATTGCAGTGAGAAGTACTG

826 TGTGGCAATATAGGGTGTACTATTGTTGCCACAAATTTAGTTCTTTCTTGTTACGTACGTACAGTTGTCAGGATG

901 CATGCATCCCCGTTGTAATGTTGGAGTACTCCATGATTTCGTTGCAATATATATATTGCCATGAGTCTAAAG
```

FIG. 15

```
                                                  M  K  M  M  S  T
1        ACCAGCACCAAGAAAACAAAAAGCATGAAGATGATGAGCACC  WGA-A
                                               M  R
1                      AATAATGAGAAAGATGATGAGCACC  WGA-D
1                CAGAAAACAAGAAGGATGAAGATGATGAGCACC  BARLEY

     R  A  L  A  L  G  A  A  A  V  L  A  F  A  A  A  T  A  Q  A
43   AGGGCCCTCGCGCTCGGCGCGGCTGCCGTCCTCGCCTTCGCCGCGGCGACCGCTCAGGCC  WGA-A
     M        T              V  F
26   ATGGCCCTTACGCTCGGCGCGGCTGTCTTCCTCGCCTTCGCCGCGGCGACCGCGCAGGCC  WGA-D
                                                            H
34   AGGGCCCTCGCTCTCGGCGCGGCCGCCGTCCTCGCCTTCGCGGCGGCGACCGCGCACGCC  BARLEY
      *       ** *           * * *          *         *  *

     Q  R  C  G  E  Q  G  S  N  M  E  C  P  N  N  L  C  C  S  Q
103  CAGAGGTGCGGCGAGCAAGGCAGCAACATGGAGTGCCCCAACAACCTCTGCTGCAGCCAG  WGA-A
86   CAGAGGTGCGGCGAGCAGGGCAGCAACATGGAGTGCCCCAACAACCTCTGCTGCAGCCAG  WGA-D
94   CAGAGGTGCGGCGAGCAGGGCAGCAACATGGAGTGCCCCAACAACCTCTGCTGCAGCCAG  BARLEY
                      *

     Y  G  Y  C  G  M  G  G  D  Y  C  G  K  G  C  Q  N  G  A  C
163  TACGGGTACTGCGGGATGGGCGGCGACTACTGCGGCAAGGGCTGCCAGAACGGCGCCTGC  WGA-A
146  TACGGGTACTGCGGCATGGGCGGCGACTACTGCGGCAAGGGCTGCCAGAACGGCGCCTGC  WGA-D
154  TACGGGTACTGCGGCATGGGCGGCGACTACTGCGGCAAGGGCTGCCAGAACGGCGCCTGC  BARLEY
                   *

     W  T  S  K  R  C  G  S  Q  A  G  G  A  T  C  T  N  N  Q  C
223  TGGACCAGCAAGCGCTGCGGCAGCCAGGCCGGCGGCGCGACGTGCACCAACAACCAGTGC  WGA-A
                                                   P        H
206  TGGACCAGCAAGCGCTGCGGCAGCCAGGCCGGCGGGGCGACGTGTCCCAACAACCACTGC  WGA-D
     Y                    T              K        P        H
214  TACACCAGCAAGCGCTGCGGCACTCAGGCCGGCGGCAAGACATGCCCTAACAACCACTGC  BARLEY
     **                   **             ***   *  ** *        *

     C  S  Q  Y  G  Y  C  G  F  G  A  E  Y  C  G  A  G  C  Q  G
283  TGCAGCCAGTACGGGTACTGCGGCTTCGGCGCCGAGTACTGCGGCGCCGGCTGCCAGGGC  WGA-A
                    H
266  TGCAGCCAGTACGGGCACTGCGGCTTCGGAGCCGAGTACTGCGGCGCCGGCTGCCAGGGC  WGA-D
              W
274  TGCAGCCAGTGGGGTTACTGCGGCTTCGGCGCCGAGTACTGCGGCGCCGGCTGCCAGGGC  BARLEY
              **  **          *

     G  P  C  R  A  D  I  K  C  G  S  Q  A  G  G  K  L  C  P  N
343  GGCCCCTGCCGCGCCGACATCAAGTGCGGCAGCCAGGCCGGCGGCAAGCTGTGCCCGAAC  WGA-A
                                         S
326  GGCCCCTGCCGCGCCGACATCAAGTGCGGCAGCCAGTCCGGCGGCAAGCTATGCCCGAAC  WGA-D
334  GGCCCCTGCCGCGCCGACATCAAGTGCGGCAGCCAGGCCGGCGGCAAGCTTTGCCCCAAC  BARLEY
                                         *              *     *
```

FIG. 16A

```
     N  L  C  C  S  Q  W  G  F  C  G  L  G  S  E  F  C  G  G  G
403 AACCTCTGCTGCAGCCAGTGGGGATTCTGCGGCCTCGGTTCCGAGTTCTGCGGCGGCGGC  WGA-A
386 AACCTCTGCTGCAGCCAGTGGGGATTCTGCGGCCTAGGTTCCGAGTTCTGCGGCGGTGGC  WGA-D
                              Y                            E
394 AACCTCTGCTGCAGCCAGTGGGGTTACTGCGGCCTCGGCTCCGAGTTCTGCGGCGAGGGC  BARLEY
                           * *         *  *                **

     C  Q  S  G  A  C  S  T  D  K  P  C  G  K  D  A  G  G  R  V
463 TGCCAGAGCGGTGCTTGCAGCACCGACAAACCGTGCGGCAAGGACGCCGGCGGCAGAGTT  WGA-A
446 TGCCAGAGCGGTGCTTGCAGCACCGACAAGCCGTGCGGCAAGGACGCCGGCGGCAGGGTT  WGA-D
           G                                     A              K
454 TGCCAGGGCGGTGCTTGCAGCACCGACAAGCCGTGCGGCAAGGCCGCCGGCGGCAAAGTT  BARLEY
          *                      *                *           **

     C  T  N  N  Y  C  C  S  K  W  G  S  C  G  I  G  P  G  Y  C
523 TGCACTAACAACTACTGTTGTAGCAAGTGGGGATCCTGTGGCATCGGCCCGGGCTATTGC  WGA-A
506 TGCACTAACAACTACTGTTGTAGCAAGTGGGGATCCTGTGGCATCGGCCCGGGCTATTGC  WGA-D
514 TGCACCAACAACTACTGCTGCAGCAAGTGGGGATCCTGTGGCATCGGCCCGGGCTACTGC  BARLEY
         *           *  *                                   *

     G  A  G  C  Q  S  G  G  C  D  G  V  F  A  E  A  I  T  A  N
583 GGTGCAGGCTGCCAGAGTGGCGGCTGCGATGGTGTCTTCGCCGAGGCCATCACCGCCAAC  WGA-A
                                   A           G
566 GGTGCAGGCTGCCAGAGCGGCGGCTGTGACGCTGTCTTTGCCGGCGCCATCACCGCCAAC  WGA-D
                                                        A
574 GGCGCAGGTTGCCAGAGCGGCGGCTGCGACGGTGTCTTCGCCGAGGCCATCGCCGCCAAC  BARLEY
      *     *        *         *  *  *      *    **      *

     S  T  L  L  Q  E  #  #
643 TCCACTCTTCTCCAAGAATGATGATCAATCTTGCTA TGGCAGTATT   GCAACGACGAATA  WGA-A
                 A
626 TCCACTCTTCTCGCAGAATGATGATCGACCTTCCTA TGGCAGTATT   GCAACGACGAATA  WGA-D
              V  A
634 TCCACTCTTGTCGCAGAATGATGAT    CTTGCTAATGGCAGTATTATTGCAACGACGAATA  BARLEY
             *  **            ****  *   *            ***

702 ATCCGTGGCAATCTCATTGCCACC TACGGTTTCCCTTGACTTACTTTTAG AGTA CT  WGA-A
685 ATCCGTGGCAGTTTCATTGCCACGTTACGGTTTCCCTTCACTTACTTTTAGCATTAGCT  WGA-D
693 ATCCGTGGCAGTTTTGTTGCCACG TACGGTCTCCCTTCACTTACTTTTAGCACTAGTC  BARLEY
               *  * **      **      *      *            *  *  ***

758 AGTCCTTAATAATTCTCTAGC TTGCAATATGATGTGCAGGTTACTGCAGCAGAAACAAAA  WGA-A
741 AGTACTTAATAATTCTCTAGC TTGCAATGTGACATGCAGGTTACTGCAGCAGAAACAAAA  WGA-D
749     CTTAATAATTCTCCAGCCTTGCAATATGACGTGCAGGTT                    BARLEY
    ****             *   *       *   **        *****************
```

FIG. 16B

```
818  TATTGCTGTCGTGCATGCATGGAAATATTGCAGTGAGAAAGTACTGTGTGGCAATATAGG  WGA-A
801  TATTGCTGTGGTACATGCATGGGAATATTGCAGTGAGAAAGTACTGTGTGGCAATATAGG  WGA-D
809           GCTACATGCATGGACATATTGCAGTGAGAA GTACTGTGTGGCAATATAGG  BARLEY
     *********** *         **               *

878  GTGTGCTATTGTTGCCGCAAATT AGTT  TTCTTGTTA TGACCT   GTTGTCAGGATGC  WGA-A
861  GTGTACTATTGTTGCCGCAAATTTAGTT  TTCTTGTTA TGACCT   GTTGTCAGGATGC  WGA-D
859  GTGTACTATTGTTGCCACAAATTTAGTTCTTTCTTGTTACGTACGTACAGTTGTCAGGATGC  BARLEY
         *           *      *    **         ***  * ***

933  ATGCATGGCTGTTGTAATGTTGGAGTACTTCGTGATTTCGTTGCAATATAT TA   CCATGGT  WGA-A
917  ATGCATCGCTGTTGTAATGTTGGAGTACTTCGTGATTTCGTTGCAATATAT TA   CCATGAG  WGA-D
921  ATGCATCCCCGTTGTAATGTTGGAGTACTCCATGATTTCGTTGCAATATATATATTGCCATGAG  BARLEY
           ** *                   * *                   *  ***     **

993  TCTCAC                                                        WGA-A
987  CATCACATCATTAACAAAA                                           WGA-D
985  TCTAAA                                                        BARLEY
     ** * **************
```

FIG. 16C

SEQUENCE LISTING ( 1 ) GENERAL INFORMATION:

( iii ) NUMBER OF SEQUENCES: 13

( 2 ) INFORMATION FOR SEQ ID NO:1:

( i ) SEQUENCE CHARACTERISTICS:
( A ) LENGTH: 15
( B ) TYPE: Amino Acid
( C ) STRANDEDNESS: Single
( D ) TOPOLOGY: Linear ( ii ) MOLECULE TYPE:
( A ) DESCRIPTION: Peptide ( iii ) HYPOTHETICAL: No ( iv ) ANTI-SENSE: No ( v ) FRAGMENT TYPE: C-terminal fragment of barley lectin ( vi ) ORIGINAL SOURCE:
( A ) ORGANISM: wheat, barley or rice
( B ) STRAIN:
( C ) INDIVIDUAL ISOLATE: BLc3
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( vii ) IMMEDIATE SOURCE:

( viii ) POSITION IN GENOME: N/A ( ix ) FEATURE:
( A ) NAME/KEY: sorting peptide for proteins
( B ) LOCATION: encoded by amino acid 172 to 186 of barley lectin cDNA
( C ) IDENTIFICATION METHOD: sequencing
( D ) OTHER INFORMATION: Sorts proteins to vacuoles ( x ) PUBLICATION INFORMATION: N/A ( xi ) SEQUENCE DESCRIPTION: SEQ ID NO: 1:

Val Phe Ala Glu Ala Ile Ala Ala Asn Ser Thr Leu Val
1 5 10

Ala Glu
15

( 2 ) INFORMATION FOR SEQ ID NO:2:

( i ) SEQUENCE CHARACTERISTICS:
( A ) LENGTH: 15
( B ) TYPE: Amino acid
( C ) STRANDEDNESS: Single
( D ) TOPOLOGY: Linear ( ii ) MOLECULE TYPE:
( A ) DESCRIPTION: Peptide ( iii ) HYPOTHETICAL: No ( iv ) ANTI-SENSE: No ( v ) FRAGMENT TYPE: C-terminal fragment of wheat lectin (WGA-A)

( vi ) ORIGINAL SOURCE:
( A ) ORGANISM: wheat
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A -continued ( I ) ORGANELLE: N/A ( v i i ) IMMEDIATE SOURCE:

( v i i i ) POSITION IN GENOME: N/A ( i x ) FEATURE:
( A ) NAME/KEY: sorting peptide for proteins
( B ) LOCATION: encoded by amino acids 172 to 186 of WGA isolectin A cDNA
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 2:

Val Phe Ala Glu Ala Ile Thr Ala Asn Ser Thr Leu Leu
1 5 10

Gln Glu
15

( 2 ) INFORMATION FOR SEQ ID NO:3:

( i ) SEQUENCE CHARACTERISTICS:
( A ) LENGTH: 15
( B ) TYPE: Amino acid
( C ) STRANDEDNESS: Single
( D ) TOPOLOGY: Linear ( i i ) MOLECULE TYPE:
( A ) DESCRIPTION: Peptide ( i i i ) HYPOTHETICAL: No ( i v ) ANTI-SENSE: No ( v ) FRAGMENT TYPE: C-terminal fragment of wheat lectin (WGA-B)

( v i ) ORIGINAL SOURCE:
( A ) ORGANISM: wheat
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: sorting peptide for proteins
( B ) LOCATION: encoded by amino acids 172 to 186 of WGA isolectin B cDNA
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 3:

Val Phe Ala Glu Ala Ile Ala Thr Asn Ser Thr Leu Leu
1 5 10

Ala Glu
15

( 2 ) INFORMATION FOR SEQ ID NO:4:

( i ) SEQUENCE CHARACTERISTICS:
( A ) LENGTH: 15
( B ) TYPE: Amino acid ( C ) STRANDEDNESS: Single
( D ) TOPOLOGY: Linear ( i i ) MOLECULE TYPE:
( A ) DESCRIPTION: Peptide ( i i i ) HYPOTHETICAL: No ( i v ) ANTI-SENSE: No ( v ) FRAGMENT TYPE: C-terminal fragment of wheat lectin
( W G A - D )

( v i ) ORIGINAL SOURCE:
( A ) ORGANISM: wheat
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: sorting peptide for proteins
( B ) LOCATION: encoded by amino acids 172 to 186 of WGA isolectin D cDNA
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 4:

```
Val Phe Ala Gly Ala Ile Thr Ala Asn Ser Thr Leu Leu
 1               5                   10

Ala Glu
    15
```

( 2 ) INFORMATION FOR SEQ ID NO:5:

( i ) SEQUENCE CHARACTERISTICS:
( A ) LENGTH: 26
( B ) TYPE: Amino acid
( C ) STRANDEDNESS: Single
( D ) TOPOLOGY: Linear ( i i ) MOLECULE TYPE:
( A ) DESCRIPTION: Peptide ( i i i ) HYPOTHETICAL: No ( i v ) ANTI-SENSE: No ( v ) FRAGMENT TYPE: C-terminal fragment of rice lectin ( v i ) ORIGINAL SOURCE:
( A ) ORGANISM: rice
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: sorting peptide for proteins ( B ) LOCATION: encoded by amino acids 175 to 199 of rice lectin cDNA
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 5:

Asp Gly Met Ala Ala Ile Leu Ala Asn Asn Gln Ser Val
1 5 10

Ser Phe Glu Gly Ile Ile Glu Ser Val Ala Glu Leu Val
15 20 25

( 2 ) INFORMATION FOR SEQ ID NO:6:

( i ) SEQUENCE CHARACTERISTICS:
( A ) LENGTH: 15
( B ) TYPE: Amino acid
( C ) STRANDEDNESS: Single
( D ) TOPOLOGY: Linear ( i i ) MOLECULE TYPE:
( A ) DESCRIPTION: Peptide ( i i i ) HYPOTHETICAL: Yes ( i v ) ANTI-SENSE: No ( v ) FRAGMENT TYPE: Hypothetical generic sequence ( v i ) ORIGINAL SOURCE:
( A ) ORGANISM: barley
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: sorting peptide for proteins
( B ) LOCATION: encoded by amino acids 172 to 186 of barley lectin cDNA
( C ) IDENTIFICATION METHOD: sequencing
( D ) OTHER INFORMATION: 4 Xaa is Gly or Glu, 7 Xaa and 8 Xaa is Ala or Thr, 13 Xaa is Val or Leu, 14 Xaa is Ala or Gln ( x ) PUBLICATION INFORMATION: N/A ( x i ) SEQUENCE DESCRIPTION: SEQ ID NO: 6:

Val Phe Ala Xaa Ala Ile Xaa Xaa Asn Ser Thr Leu Xaa Xaa
1 5 10

Glu
15

( 2 ) INFORMATION FOR SEQ ID NO:7:

( i ) SEQUENCE CHARACTERISTICS:
( A ) LENGTH: 45
( B ) TYPE: Nucleic Acid
( C ) STRANDEDNESS: Single
( D ) TOPOLOGY: Linear ( i i ) MOLECULE TYPE:
( A ) DESCRIPTION: Nucleic Acid ( i i i ) HYPOTHETICAL: No ( i v ) ANTI-SENSE: No ( v ) FRAGMENT TYPE: DNA encoding sorting protein for barley lectin ( v i ) ORIGINAL SOURCE:
( A ) ORGANISM: barley
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: DNA encoding sorting signal peptide for proteins
( B ) LOCATION: barley lectin DNA
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 7:

GTCTTCGCCG AGGCCATCGC CGCCAACTCC ACTCTTGTCG CAGAA 45

( 2 ) INFORMATION FOR SEQ ID NO:8:

( i ) SEQUENCE CHARACTERISTICS:
( A ) LENGTH: 45
( B ) TYPE: Nucleic Acid
( C ) STRANDEDNESS: Single
( D ) TOPOLOGY: Linear ( i i ) MOLECULE TYPE:
( A ) DESCRIPTION: Nucleic Acid ( i i i ) HYPOTHETICAL: No ( i v ) ANTI-SENSE: No ( v ) FRAGMENT TYPE: DNA encoding sorting signal for WGA-A wheat lectin ( v i ) ORIGINAL SOURCE:
( A ) ORGANISM: wheat
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: DNA encoding sorting peptide for proteins
( B ) LOCATION: wheat isolectin A
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 8:

GTCTTCGCCG AGGCCATCAC CGCCAACTCC ACTCTTCTCC AAGAA 45

( 2 ) INFORMATION FOR SEQ ID NO:9:

( i ) SEQUENCE CHARACTERISTICS:
( A ) LENGTH: 45
( B ) TYPE: Nucleic Acid
( C ) STRANDEDNESS: Single
( D ) TOPOLOGY: Linear ( i i ) MOLECULE TYPE:
( A ) DESCRIPTION: Nucleic Acid ( i i i ) HYPOTHETICAL: No ( i v ) ANTI-SENSE: No ( v ) FRAGMENT TYPE: DNA encoding sorting signal for WGA-D wheat lectin ( v i ) ORIGINAL SOURCE:
( A ) ORGANISM: wheat
( B ) STRAIN:
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: DNA encoding sorting peptide for proteins
( B ) LOCATION: WGA isolectin D
( C ) IDENTIFICATION METHOD: sequencing
( D ) OTHER INFORMATION: Sorts proteins to vacuoles ( x ) PUBLICATION INFORMATION: N/A ( x i ) SEQUENCE DESCRIPTION: SEQ ID NO: 9:

GTCTTTGCCG GCGCCATCAC CGCCAACTCC ACTCTTCTCG CAGAA 45

( 2 ) INFORMATION FOR SEQ ID NO:10:

( i ) SEQUENCE CHARACTERISTICS:
( A ) LENGTH: 16
( B ) TYPE: Nucleic Acid
( C ) STRANDEDNESS: Single
( D ) TOPOLOGY: Linear ( i i ) MOLECULE TYPE:
( A ) DESCRIPTION: Synthetic Nucleotide ( i i i ) HYPOTHETICAL: No ( i v ) ANTI-SENSE: No ( v ) FRAGMENT TYPE: N/A ( v i ) ORIGINAL SOURCE: N/A
( A ) ORGANISM: N/A
( B ) STRAIN: N/A
( C ) INDIVIDUAL ISOLATE: N/A
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: primer
( B ) LOCATION: N/A
( C ) IDENTIFICATION METHOD: N/A
( D ) OTHER INFORMATION: N/A ( x ) PUBLICATION INFORMATION: N/A ( x i ) SEQUENCE DESCRIPTION: SEQ ID NO: 10:

CGGCGGCTGC GACGGT 16

( 2 ) INFORMATION FOR SEQ ID NO:11:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i i ) MOLECULE TYPE:
( A ) DESCRIPTION: Synthetic Nucleotide ( i i i ) HYPOTHETICAL: No ( i v ) ANTI-SENSE: No ( v ) FRAGMENT TYPE: N/A ( v i ) ORIGINAL SOURCE: N/A
( A ) ORGANISM: N/A
( B ) STRAIN: N/A
( C ) INDIVIDUAL ISOLATE: N/A
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: primer
( B ) LOCATION: N/A
( C ) IDENTIFICATION METHOD: N/A
( D ) OTHER INFORMATION: N/A ( x ) PUBLICATION INFORMATION: N/A ( x i ) SEQUENCE DESCRIPTION: SEQ ID NO: 11:

GATGATCTTG CTAATGGCAG 20

( 2 ) INFORMATION FOR SEQ ID NO:12:

( i ) SEQUENCE CHARACTERISTICS:
( A ) LENGTH: 22
( B ) TYPE: Amino Acid
( C ) STRANDEDNESS: Single
( D ) TOPOLOGY: Linear ( i i ) MOLECULE TYPE:
( A ) DESCRIPTION: Peptide ( i i i ) HYPOTHETICAL: No ( i v ) ANTI-SENSE: No ( v ) FRAGMENT TYPE: Tobacco -1,3-glucanase ( v i ) ORIGINAL SOURCE:
( A ) ORGANISM: N. tabacum
( B ) STRAIN: N/A
( C ) INDIVIDUAL ISOLATE: N/A -continued ( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE:

( v i i i ) POSITION IN GENOME: N/A ( i x ) FEATURE:
( A ) NAME/KEY: -glucanase peptide
( B ) LOCATION: N/A
( C ) IDENTIFICATION METHOD: sequencing
( D ) OTHER INFORMATION: N/A ( x ) PUBLICATION INFORMATION: N/A ( x i ) SEQUENCE DESCRIPTION: SEQ ID NO: 12:

```
Val Ser Gly Gly Val Trp Asp Ser Ser Val Glu Thr Asn Ala Thr Ala
                5                   10                  15

Ser Leu Val Ser Glu Met
            20
```

( 2 ) INFORMATION FOR SEQ ID NO:13:

( i ) SEQUENCE CHARACTERISTICS:
( A ) LENGTH: 23
( B ) TYPE: Amino Acid
( C ) STRANDEDNESS: Single
( D ) TOPOLOGY: Linear ( i i ) MOLECULE TYPE:
( A ) DESCRIPTION: Peptide ( i i i ) HYPOTHETICAL: No ( i v ) ANTI-SENSE: No ( v ) FRAGMENT TYPE: Tobacco 1,3-glucanase ( v i ) ORIGINAL SOURCE:
( A ) ORGANISM: N. plumbaginifolia
( B ) STRAIN: N/A
( C ) INDIVIDUAL ISOLATE:
( D ) DEVELOPMENTAL STAGE: N/A
( E ) HAPLOTYPE: N/A
( F ) TISSUE TYPE: N/A
( G ) CELL TYPE: N/A
( H ) CELL LINE: N/A
( I ) ORGANELLE: N/A ( v i i ) IMMEDIATE SOURCE: N/A ( v i i i ) POSITION IN GENOME: N/A ( i x ) FEATURE:
( A ) NAME/KEY: -glucanase peptide
( B ) LOCATION: N/A
( C ) IDENTIFICATION METHOD: sequencing
( D ) OTHER INFORMATION: N/A ( x ) PUBLICATION INFORMATION: N/A ( x i ) SEQUENCE DESCRIPTION: SEQ ID NO: 13:

```
Phe Ser Asp Arg Tyr Trp Asp Ile Ser Ala Glu Asn Asn Ala Thr
                5                   10                  15

Ala Ala Ser Leu Ile Ser Glu Met
                20
```

DNA ENCODING POLYPEPTIDES ENABLING SORTING OF PROTEINS TO VACUOLES IN PLANTS

CROSS-REFERENCE TO RELATED APPLICATION

This application is a continuation-in-part of application Ser. No. 07/917,665, filed Jul. 20, 1992 now U.S. Pat. No. 5,276,269 (which is a continuation of Ser. No. 07/406,318, filed in Sep. 12, 1989, now abandoned); and a continuation-in-part of Ser. No. 791,930, filed Nov. 12, 1991, now U.S. Pat. No. 5,360,726, which is a continuation-in-part of Ser. No. 07/612,200, filed Nov. 13, 1990, now abandoned, which is a continuation-in-part of application Ser. No. 07/406,318, filed Sep. 12, 1989, now abandoned.

BACKGROUND OF THE INVENTION (1) Field of the Invention

The present invention relates to cDNA encoding polypeptides which when attached to the C-Terminal region of a protein enables sorting of proteins to the vacuoles in plants. In particular, the present invention relates to polypeptides which enables the sorting of lectins, which are insecticidal polypeptides, to the vacuole of a plant.

(2) Prior Art

In eukaryotes, proteins of the endoplasmic reticulum (ER), Golgi, lysosomes, vacuoles, plasma membrane, and cell wall are derived from a subset of proteins that enter the secretory pathway. Proteins are targeted to the secretory pathway by an N-terminal hydrophobic signal sequence which mediates a transmembrane translocation from the cytosol to the lumen of the endoplasmic reticulum. Following proteolytic cleavage of the signal sequence, some secretory proteins undergo further post-translational processing in the ER and Golgi network (Blobel, G., and Dobberstein, D., J. Cell Biol. 67, 835–851 (1975)). Proteins traversing the secretory pathway are believed to be sorted to their respective compartments by selective retention or targeting information contained in their molecular structures (Rothman, J. E., Cell 50, 521–522 (1987)). Proteins lacking specific sorting determinants follow a default pathway and are consequently secreted toward the cell surface (Rothman, J. E., Cell 50, 521–522 (1987); Wieland, F. T., et al., Cell 50, 289–300 (1987); Dorel, C., et al., J. Cell Biol. 108, 327–337 (1989); and Denecke, J., et al., Plant Cell 2, 51–59 (1990)).

A secondary sorting signal that mediates a targeting process involves either a post-translational modification of the protein or depends upon primary, secondary, or tertiary structural elements within the polypeptide (Verner, K., et al., Protein translocation across membranes. 241, 1307–1313 (1988)). The most well characterized sorting process is the mannose-6-phosphate dependent sorting of mammalian lysosomal enzymes (Kornfeld, S., et al., Ann. Rev. Cell Biol. 5, 483–525 (1989)). The active sorting of these enzymes to the lysosome is dependent on the modification of specific glycans with mannose-6-phosphate and the binding of the modified glycan to mannose-6-phosphate receptors in the trans-Golgi network (reviewed in Kornfeld, S., and Mellman, I., Ann. Rev. Cell Biol., 5, 483–525 (1989)). However, there is evidence for the existence of a mannose-6-phosphate independent system for the sorting of some mammalian lysosomal enzymes (Gabel, C. A., et al., Proc. Natl. Acad. Sci. U.S.A. 80, 775–779 (1983)).

In yeast and plants, N-linked glycans are not necessary for the correct transport and sorting of secretory proteins to vacuoles (Stevens, T. H., et al., Cell 30, 439–448 (1982); Voelker, T. A., et al., Plant Cell 1, 95–104 (1989); Wilkins, T. A., et al., Plant Cell 2, 301–313 (1990); and Sonnewald, U., et al., Plant Cell 2, 345–355 (1990)). Therefore, it appears that targeting of proteins to vacuoles in yeast and plants is independent of post-translational modifications to oligosaccharide side-chains and may be dependent upon elements within the polypeptide. Such peptide sorting determinant is identified for the yeast vacuolar carboxypeptidase Y (CPY). It has been demonstrated that the amino-terminal propeptide of CPY fused with the secreted enzyme invertase, contains the sorting signal of CPY (Johnson, L. M., et al., Cell 28, 875–885 (1987); and Valls, L. A., et al., Cell 48, 887–897 (1987)). A detailed mutational analysis of the amino-terminal propeptide determined that the tetrapeptide QRPL functions as a vacuolar sorting signal. Interestingly, the context in which the QRPL sequence is presented affects the efficiency of targeting, inferring the involvement of secondary structural elements in the sorting mechanism of CPY (Valls, L. A., et al., J. Cell Biol. 111, 361–368 (1990)). A sorting determinant was identified in the amino-terminal propeptide of another yeast vacuolar enzyme, proteinase A (Klionsky, D. J., et al., Mol. Cell Biol. 3, 2105–2116 (1988)), which is sufficient to redirect the normally secreted enzyme invertase to the yeast vacuole. However, currently no consensus sequence or common structural determinant has been demonstrated for targeting of yeast vacuolar proteins, suggesting that a diverse array of factors are involved in the sorting process.

It has been also shown that the plant vacuolar protein phytohemagglutinin-L (PHA), a lectin of Phaseolus vulgaris, is correctly processed and sorted to the yeast vacuole (Tague, B. W., et al., J. Cell Biochem. Suppl. 13D, 230 (1989)). Deletion analysis of PHA localized the vacuolar sorting domain within the amino-terminal portion of mature PHA (Tague, B. W., et al., Plant Cell 2, 533–546 (1990)). This domain contains a yeast-like targeting tetrapeptide sequence (LQRD), that is sufficient to target PHA-invertase hybrid proteins to the yeast vacuole (Tague, B. W., et al., Plant Cell 2, 533–546 (1990)). It should be noted however, that the same PHA-invertase fusion proteins were not successfully targeted to vacuoles in Arabidopsis thaliana protoplasts (Chrispeels, M. J., Ann. Rev. Plant Physiol. Plant Molec. Biol. 42, (1991)). Therefore, this sorting determinant contains enough information for vacuolar sorting in yeast, but appears to lack the necessary information for efficient targeting in plants, suggesting that vacuolar sorting signals in yeast and plants are dissimilar.

The ability to sort proteins to the vacuoles of plants is very useful. The result is that the fruits or leaves contain more protein which for edible plants is important to the food value of the plant or which contain antimicrobial agents such as lectins which are active against fungi and insects which attack the plant.

Several publications describe the sequencing of the lectins and the cDNA encoding the lectins for wheat, barley and rice. These publications are Raikhel, et al., Proc. Natl. Acad. Sci. 84, 6745–6749 (1987); Smith et al., Plant Molecular Biology 13, 601–603 (1989); Plant Physiology 91, 124–129 (1989); and Wilkins et al 1, 541–549 (1989). The structure of the lectins expressed by the genes was described with the peptide residues described herein; however, no utility for the residues was disclosed. The residues were not isolated from the lectin protein encoded by the cDNA.

OBJECTS

It is therefore an object to provide a polypeptide which enables the sorting of lectin and other proteins to the vacuoles in plants, particularly in tobacco plants. In particular, it is an object of the present invention to provide a protein which directs lectins to the vacuoles of plants. It is further an object of the present invention to provide a method for directing the proteins to the vacuoles using a C-terminal polypeptide. These and other objects will become increasingly apparent by reference to the following description and the drawings.

IN THE DRAWINGS

FIG. 4 shows an electrophoresis gel for WT (A) and ctpp$^-$(B) RNA in media and in suspension cultured cells.

FIG. 5 shows an electrophoresis gel for WT (A) and ctpp$^-$(B) in protoplasts isolated from transgenic tobacco and in the media.

FIG. 6 shows an amino acid sequence comparison of carboxyl-terminal propeptides of gramineae lectins and tobacco beta-1,3-glucanases. SEQ ID NOS: 12 and 13 also show the amino acids for the tobacco beta-1,3-glucanases. In FIG. 6 the three letter codes are:

D=Asp
N=Asn
E=Glu
G=Gly
Q=Gln
H=His
R=Arg
T=Thr
A=Ala
P=Pro
Y=Tyr
V=Val
M=Met
C=Cys
I=Ile
L=Leu
F=Phe
K=Lys
S=Serine
W=Trp FIG. 7 shows a model for barley lectin sorting in the trans-Golgi network.

FIG. 8 is a schematic representation of proBL/Cuc Chit Fusion Proteins. A. The preproprotein of barley lectin consists of a signal sequence (box with dark hatched lines), a mature 18 kD subunit (open box), and the CTPP (box with light hatched lines). The insert represents the 15-amino acid CTPP propeptide (lightly shaded box), Gly (G) is the last amino acid from the carboxyl-terminus of the mature BL preceding the CTPP. Leu (L) and Glu (E) (open box) were added by introduction of a XhoI restriction site (see Methods).

B. (1) The preprotein of Cuc Chit contains a signal sequence (shaded box) and the mature 28-kD polypeptide (solid black box). (2) Cuc Chit is fused with the 23-kD glycosylated BL proprotein (Cuc Chit-proBL). (3) Cuc Chit is fused with the mature 18-kD BL subunit (Cuc Chit-BL). (4) Cuc Chit is fused with the glycosylated CTPP (Cuc Chit-CTPP). (5) Cuc Chit-CTPP fusion protein that has been modified by site-directed mutagenesis to prevent core glycosylation of the CTPP (Cuc Chit-CTPP[gly$^-$]).

Figure 9:
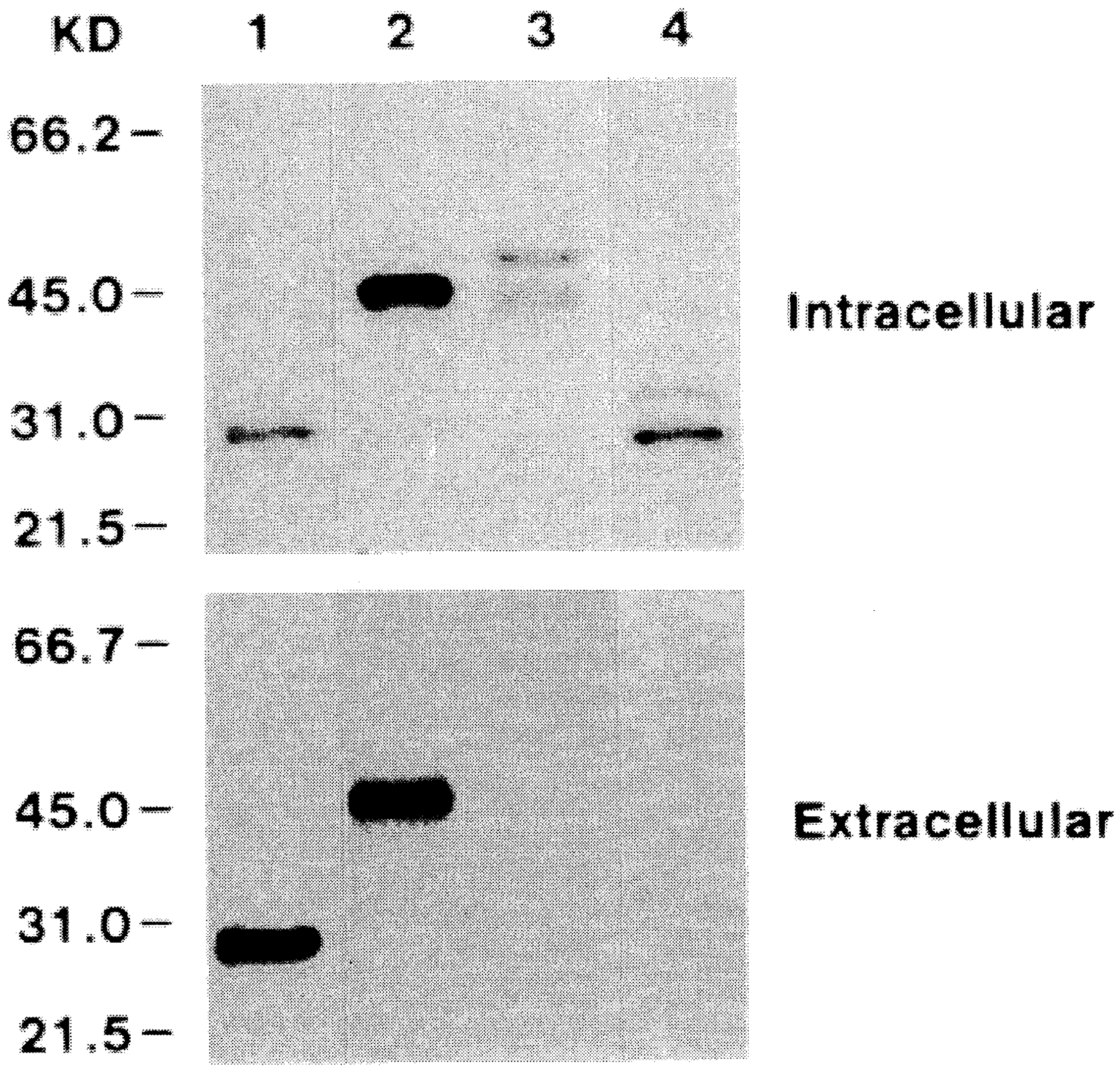

FIG. 9 is an analysis of transiently expressed Cuc Chit fusion proteins in tobacco protoplasts. Cuc Chit/pGA643 constructs were introduced into tobacco protoplasts by PEG-mediated DNA uptake. Immunopurified proteins from the intracellular and extracellular fractions of pulse labeled tobacco protoplasts expressing, Cuc Chit (lane 1), Cuc Chit-BL (lane 2), Cuc Chit-proBL (lane 3), and Cuc Chit-CTPP (lane 4) were electrophoresed on 12.5% SDS-polyacrylamide gels and visualized by fluorography. The migration of molecular mass markers (kD) is represented on the left.

FIG. 10 is a pulse-chase labeling experiment of tobacco protoplats expressing Cuc Chit and Cuc Chit-CTPP fusion proteins.

A. Immunopurified intracellular and extracellular proteins from tobacco protoplasts expressing Cuc Chit.

B. Immunopurified intracellular and extracellular proteins from tobacco protoplasts expressing Cuc Chit-CTPP.

Protoplasts were pulse labeled for 2.5 hours and chased for 8 hours. protein extracts were prepared from the protoplats and incubation media at specified intervals during the chase as indicated. Radiolabeled proteins were immunoprecipitated with anti-Cuc Chit antisera and analyzed by SDS-PAGE and fluorography. Molecular mass markers (kD) are indicated on the left.

Figure 11:
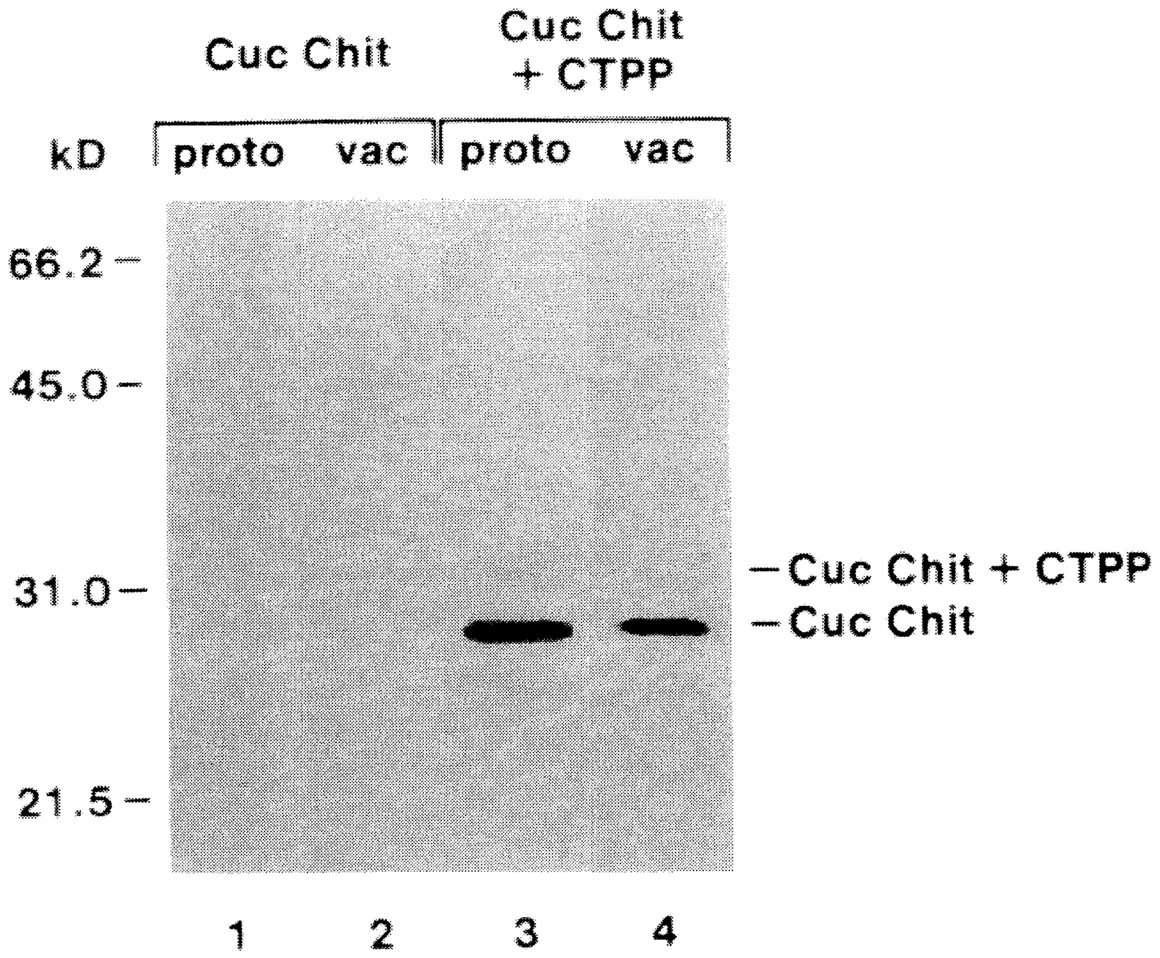

FIG. 11 is a localization of the processed form of the Cuc Chit-CTPP fusion protein in the vacuoles of Cuc Chit-CTPP transgenic tobacco protoplasts. Total protein from protoplasts and isolated vacuoles were separated by electrophoresis on a 12.5% SDS-polyacrylamide gel, and electroblotted onto Immobilon-P membrane. Immunodetection of Cuc Chit was performed with anti-Cuc Chit antisera as described in Methods. Equal amounts of soluble vacuole proteins in the protoplast and vacuole fractions, relative to amannosidase activity, were loaded per lane. The sizes of molecular mass standards (kD) are shown on the left.

FIG. 12 shows immunocytochemical localization of Cuc Chit and Cuc Chit-CTPP Fusion in transgenic tobacco cells.

(A) and (C) Thin sections of transgenic tobacco leaves expressing Cuc Chit (A) and Cuc Chit-CTPP (C) treated with anti-Cuc Chit antisera.

(B) and (D) Thin sections of transgenic tobacco leaves expressing Cuc Chit (B) and Cuc Chit-CTPP (D) treated with nonimmune sera.

Antibody binding was visualized by protein A-gold (15 nm). Gold label (arrow) is found exclusively in the cell wall of tobacco plants transformed with Cuc Chit transcript (panel A) and within the vacuoles of transgenic Cuc Chit-CTPP tobacco plants (panel C). Bars=0.5 μm. The abbreviations used are: CW, cell wall; V, vacuole.

Figures 13A, 13B:
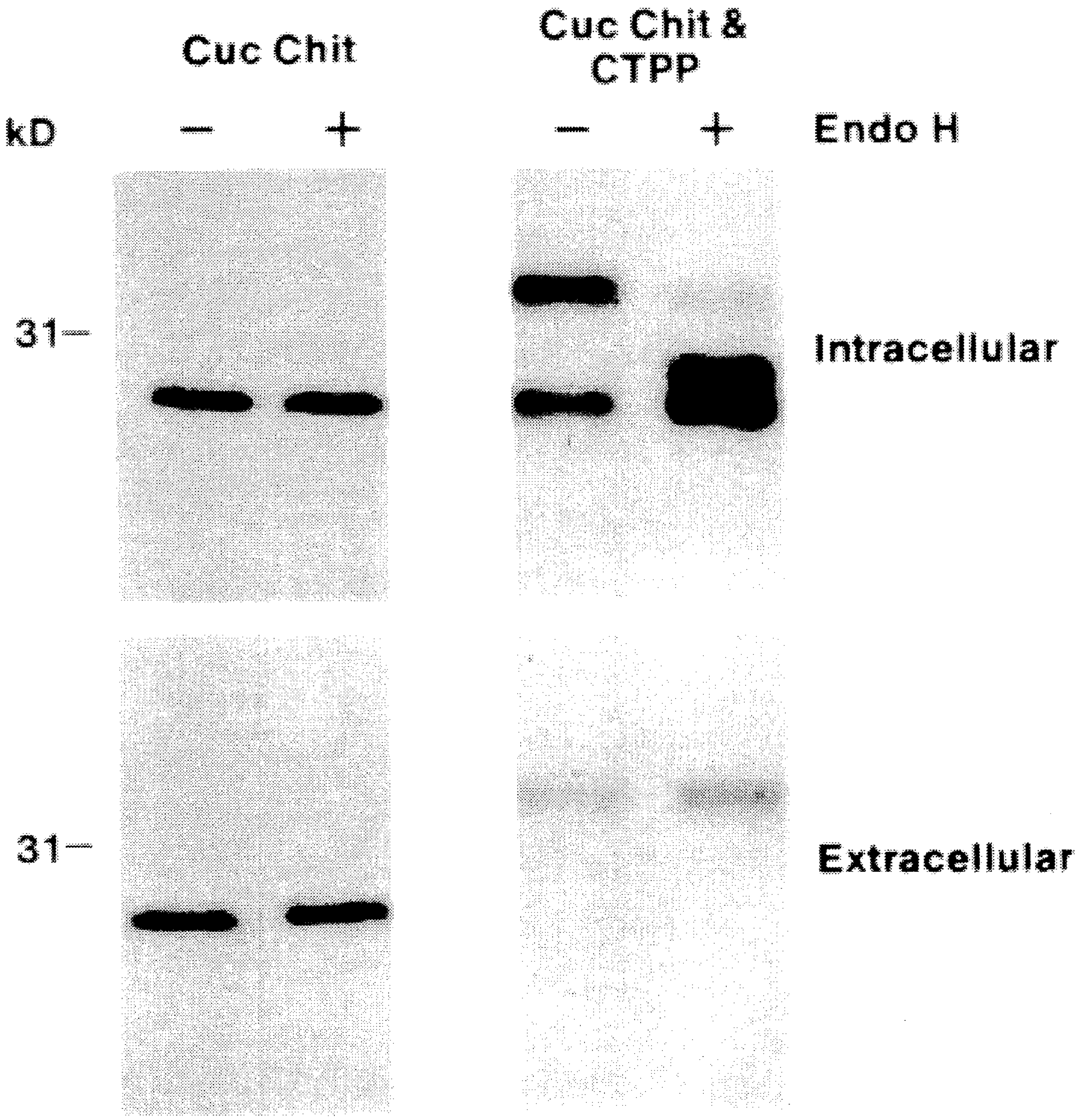

FIG. 13 shows endo H digestion of radiolabeled Cuc Chit and Cuc Chit-CTPP fusion protein. Radiolabeled proteins were immunopurified from the intracellular and extracellular fractions of tobacco protoplasts expressing Cuc Chit and Cuc Chit-CTPP. Duplicate samples were incubated at 37° C. for 18 hours in the absence or presence of endo H prior to analysis by SDS-PAGE and fluorography.

Figures 14A, 14B:
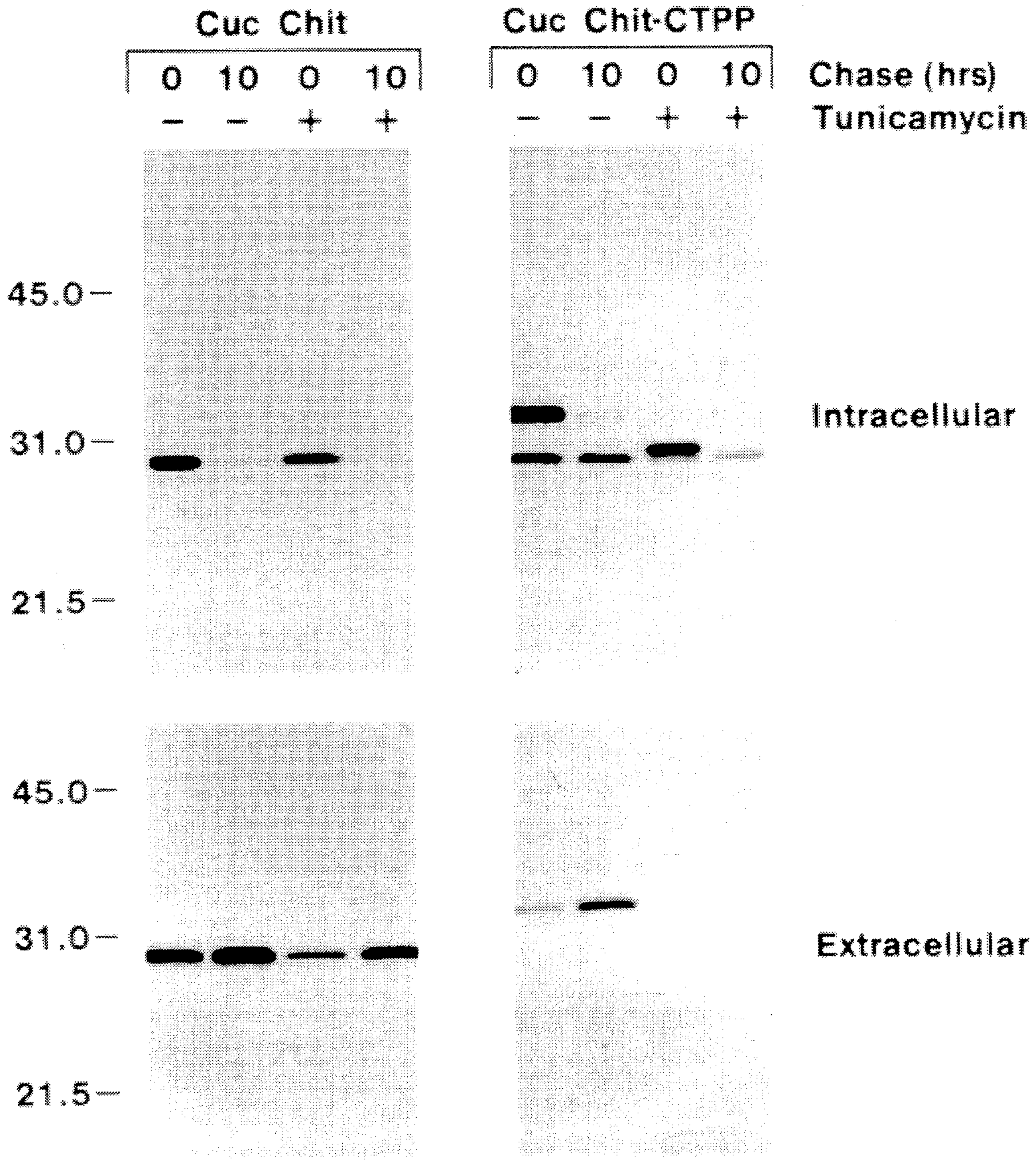

FIG. 14 shows the effect of core glycosylation inhibition on sorting of the Cuc Chit-CTPP proprotein to the vacuole.

Protoplasts expressing Cuc Chit and Cuc Chit-CTPP were labeled in the presence or absence of tunicamycin and $^{35}S$-labeled proteins were chased for 10 hours with excess Met/Cys. Proteins were immunopurified with anti-Cuc Chit antisera from protoplasts and incubation media, and analyzed by SDS-PAGE and fluorography. The migration of molecular mass standards (kD) is shown on the left.

FIG. 15 shows nucleotide and deduced amino acid sequence of barley lectin cDNA clone BLc3. The deduced amino acid sequence is from the first methionine residue and numbered along the right margin. The signal sequence, broken underline, and carboxy-terminal extension, double underline which is the sequence encoding the sorting peptide, are not present in the mature protein. The single potential asparagine-linked glycosylation site is designated with asterisks. Two stop codons at the end of the coding region are indicated with squares. The four potential polyadenylation signals are underlined. An extensive poly $A^+$ tail is not present, so the actual site of polyadenylation is unknown.

FIG. 16 illustrates the complete nucleotide and amino acid sequences of full-length cDNA clones encoding wheat germ aggutinin isolectins A (WGA-A) and D (WGA-D) and barley lectin. Positions with differences in the nucleotide sequence of any of the three sequences are marked with asterisks (*) and the nucleotides are presented in bold-face type. The amino acid sequence derived from translation of WGA-A is shown in one-letter code above the corresponding codon. Amino acids are also indicated at positions where there are differences between the isolectins. As can be seen from FIG. 2, there are significant differences between barley lectin and the wheat germ lectins.

GENERAL DESCRIPTION

The present invention relates to a DNA encoding a sorting polypeptide selected from the group consisting of GTCTTCGCCGAGGCCATCACCGCCAAC TCCACTCTTCTCCAAGAA (WGA-A); GTCTTTGCCGGCGCCATCACCGCCAAC TCCACTCTTCTCGCAGAA (WGA-D); and GTCTTCGCCGAGGCCATCGCCGCCAAC TCCACTCTTGTCGCAGAA (Barley) as set forth in SEQ ID NOS: 7, 8 and 9. The isolation of the DNA and the polypeptide are disclosed in application Ser. No. 07/406,318, filed Sep. 12, 1989 and the disclosure of this application is incorporated herein by reference. FIGS. 15 and 16 herein show the complete DNA encoding the WGA-A; WGA-D and barley lectins.

The present invention relates also to a substantially pure C-terminal polypeptide enabling sorting of lectin to vacuoles in plants which comprises:

$VFAX_1AIX_2X_3NSTLX_4X_5E$, in which is SEQ ID NO: 6 wherein $X_1$ is selected from the group consisting of G and E, $X_2$ and $X_3$ are selected from the group consisting of A and T, $X_4$ is selected from the group consisting of V and L, and $X_5$ is selected from the group consisting of A and Q.

The present invention also relates to a method of sorting proteins to the vacuoles in plants which comprises incorporating the polypeptide $VFAX_1AIX_2X_3NSTLX_4X_5E$, which is SEQ ID NO: 6 onto the C-terminal portion of the protein.

The present invention particularly relates to a substantially pure C-terminal polypeptide enabling sorting of barley lectin to vacuoles in plants which comprises VFAEH1AANSTLVAE, which is SEQ ID NO: 1

Further, the present invention relates to a method of enabling sorting of proteins to the vacuoles in plants which comprises incorporating the polypeptide VFAEIAASTLVAE (SEQ ID NO: 1) onto the C-terminal portion of the protein. The preferred protein is a lectin, particularly barley lectin.

Barley lectin is synthesized as a preproprotein with a glycosylated carboxyl-terminal propeptide (CTPP) which is removed prior to or concomitant with deposition of the mature protein in vacuoles. Expression of a cDNA clone encoding barley lectin in transformed tobacco plants results in the correct processing, maturation and accumulation of active barley lectin in vacuoles as described in application Ser. No. 07/406,318. The glycan of the propeptide is not essential for vacuolar sorting, but may influence the rate of post-translational processing. To determine the functional role of the CTPP in processing, assembly and sorting of barley lectin to vacuoles, a mutant barley lectin cDNA clone lacking the 15 amino acid CTPP was prepared. The CTPP deletion mutant of barley lectin was expressed in tobacco protoplasts, suspension-cultured cells and transgenic plants. In all three systems, the wild-type barley lectin was sorted to vacuoles, whereas mutant barley lectin ($CTPP^-$) secreted to the incubation media. It was concluded that the carboxyl-terminal domain of the barley lectin proprotein was necessary for the efficient sorting of this protein to plant cell vacuoles.

Gramineae lectins are vacuolar proteins which are initially synthesized as glycosylated 23 kD polypeptides which dimerize within the lumen of the ER to form an active N-acetylglucosamine (GlcNac)-binding proprotein (Mansfield, M. A., et al., Planta 173, 482–489 (1988)). During transport or after arrival in the vacuoles, the glycosylated carboxyl-terminal propeptide (CTPP) is removed from the proprotein to yield the mature lectin. A transgenic plant system was used to define and characterize the molecular mechanisms that mediate the processing and vacuolar sorting of barley lectin. As a first step, it was demonstrated that barley lectin was correctly assembled, processed and targeted to vacuoles in transgenic tobacco (U.S. Ser. No. 406,318). A functional analysis of the carboxyl-terminal propeptide N-linked glycan revealed that although the glycan is not essential for processing and vacuolar sorting of the barley lectin in tobacco, the presence of the glycan does modulate the rate of processing of the propeptide.

Although the primary sequences of the carboxyl-terminal propeptides of wheat germ agglutinin (WGA), rice lectin and barley lectin are not conserved, these CTPPs share the potential to form amphipathic alpha-helices (Wilkins, T. A., et al., Plant Cell 1, 541–549 (1989)). Amphipathic alpha-helices are believed to function as targeting signals in mitochondrial protein import as well as mediating other protein-protein interactions (Verner, K., et al., Protein translocation across membranes 241, 1307–1313 (1988)). In the present invention the analysis of the functional role of the carboxyl-terminal propeptide by examining the assembly and sorting of a barley lectin mutant lacking the carboxyl-terminal propeptide has been examined. Transient expression and stably transformed suspension-cultured cell systems were established in addition to using transgenic plants to facilitate the analysis of the vacuolar sorting of barley lectin. Using these three systems it was determined that the 15 amino acid carboxyl-terminal propeptide domain was necessary for correct sorting of barley lectin to the vacuole.

SPECIFIC DESCRIPTION

The following Example 1 shows the method and results with barley lectin sorting to the vacuoles.

EXAMPLE 1

METHODS

Preparation of Barley Lectin Propeptide Deletion Mutants

Nucleotides 607 to 651 of the barley lectin cDNA (Ser. No. 07/406,318), which encodes the carboxyl-terminal propeptide of the barley lectin proprotein, were deleted by site-directed mutagenesis (Kunkel, T. A., et al., Methods Enzymol. 154, 367–382 (1987)). Uracil-containing single stranded wt barley lectin cDNA (from application Ser. No. 406,318) was prepared from bacteriophage M13K07 grown on the host dut ung $F^+$ *Escherichia coli* strain CJ236 harboring wt barley lectin cDNA in PUC 118 (Vieira, J., et al., Methods Enzymol. 153, 3–11 (1987)). The synthetic mutagenic oligonucleotide, 5'CGGCGGCTGCGACGGT/GATGATCTTGCTAATGGCAG-3' (nt 591 to 606/nt 652 to 672), (SEQ ID NO: 10 and 11 respectively), was annealed to the uracil-containing single stranded template and used to prime second-strand synthesis by T4 DNA polymerase (New England BioLabs). The CTPP deletion mutants of barley lectin were identified and selected as described in Ser. No. 406,318, subcloned into the binary plant expression vector pGA642 (An, G., et al., Plant Molec. Biol. Manual A3, 1–19 (1988)) and mobilized into the *E. coli* strain DH5a. Unless otherwise noted, all standard recombinant DNA techniques used were as described by Maniatis et al (Maniatis, T., et al., Molecular Cloning: A Laboratory Manual. Cold spring Harbor Laboratory Press, Cold Spring Harbor, N.Y. (1982)). All reagents, unless specified were purchased from Sigma Chemical Co., St. Louis, Mo.

Tobacco Suspension-Cultured Cell and Shoot Tissue Culture

*Nicotiana tabacum* suspension-cultured (NT) cells were maintained in liquid Murashige and Skoog medium (MS) (Murashige, T., et al., Physiol. Plant. 15, 473–497 (1962)) supplemented with 0.2 mg/L 2,4-D (MS 0.2 mg/L 2,4-D) at 28° C. with shaking in a gyratory shaker at 150 rpm. Suspension cells were subcultured weekly with a 5% inoculum to fresh media. Axenic shoot cultures of *N. tabacum* (cv Wisconsin 38) were maintained and propagated by node cuttings on solid MS medium.

Transient Gene Expression System in Tobacco Suspension Protoplasts

Protoplasts were prepared from 3-day NT cell cultures. NT cells were collected by centrifugation at 50×g for 5 min at room temperature. The cell pellet was resuspended and digested in MS 0.2 mg/L 2,4-D with 1.0% cellulase Onozuka R10, 0.5% macerozyme R10 (Yakult Honsha Co., Ltd., Japan), 0.1% BSA and 0.4M sucrose at 28° C. for 4 hours with gentle shaking on a gyratory shaker at 75 rpm. Protoplasts were filtered through a 90 μm steel mesh screen and purified by centrifugation in Babcock bottles (Baxter Scientific Products, McGaw Park, Ill.) at 350×g for 10 minutes at room temperature. The protoplasts were recovered from the floating band and diluted in W5 solution [145 mM NaCl, 125 mM $CaCl_2 2H_2O$, 5 mM KCl, 5 mM glucose pH 5.6] (Negrutiu, I., et al., Plant Mol. Biol. 8, 363–373 (1987)) and incubated at room temperature for 30 minutes. Viable protoplasts were visualized by fluorescein diacetate staining and the yields quantitated using a hemocytometer counting chamber.

Protoplasts were collected by centrifugation at 50×g for 10 minutes and resuspended to a final concentration of $1.7\times10^6$ viable protoplasts per ml with MaMg solution [0.4M mannitol, 15 mM $MgCl_2$, 3 mM morpholinoethanesulphonic acid (MES)-KOH pH 5.6] (Negrutiu, I., et al., Plant Mol. Biol. 8, 363–373 (1987)). Prior to adding plasmid DNA, $5\times10^5$ protoplasts were aliquoted to 15 ml polypropylene tubes (300 ul of a $1.7\times10^6$ protoplasts per ml suspension per tube) and were subjected to a 45° C. heat shock for 5 minutes. After cooling to room temperature, a mixture of 20 ug of CsCl-purified pGA643 constructs (no plasmid in negative control), and 50 ug sheared salmon sperm DNA was added to the protoplast suspension. The protoplast/plasmid DNA mixture was brought to a final concentration of 28% Polyethylene Glycol (PEG)-4000 with a solution containing 40% PEG 4000, 0.4M mannitol, 100 mM $Ca(NO_3)_2.4H_2O$, 10 mM N-2-hydroxyethylpiperazine-N'-2-ethanesulfonic acid (HEPES)-KOH pH 7.0 (Negrutiu, I., et al., Plant Mol. Biol. 8, 363–373 (1987)). After incubating at room temperature for 30 minutes, the protoplast/DNA/PEG mixture was slowly diluted with 12 volumes of W5 solution over a period of 15 minutes as described by Damm et al (Damm, B., et al., Mol. Gen. Genet. 217, 6–12 (1989)). The protoplasts were collected by centrifugation at 50×g for 10 minutes at room temperature and the protoplast pellet was resuspended in 2.5 ml MS 0.2 mg/L 2,4-D, and 0.4M mannitol to a final density of $2.0\times10^5$ protoplast per ml and transferred to 80×15 mm petri plates.

To examine expression of the barley lectin constructs, the transiently transformed NT protoplasts were incubated for 12 hours in the presence of 200 uCi ["Expre$^{35}$S$^{35}$S" protein labeling mixture, (NEN Research Products), *E. coli* hydrolysate containing a mixture of 77% L-[$^{35}$S]-methionine and 18% L-[$^{35}$S]-cysteine in 50 mM tricine, 10 mMbetaME buffer;-specific activity 1000–1100 Ci/mmol] ($^{35}$S-met/cys). After labeling, the protoplasts were separated from the culture media by centrifugation at 50×g for 10 minutes at room temperature. The protoplast pellet was resuspended in 200 ul extraction buffer [50 mM Tris-acetate pH 5.0, 100 mM NaCl, 0.6% triton X-100 and 0.6 mM dithiothreitol]. The lysate was cleared of insoluble debris by centrifugation at 16,000×g for 5 minutes at 4° C., frozen in liquid nitrogen and stored at −70° C. The culture media (2.5 ml) was filtered to remove any remaining protoplasts as described in Wilkins et al (Wilkins, T. A., et al., Plant Cell 2, 301–313 (1990)). Proteins in the culture media were precipitated with ammonium sulfate at 70% saturation at 4° C. or 2 hours and then collected by centrifugation at 10,000×g for 10 minutes at 4° C. The culture media protein pellet was resuspended in 200 ul extraction buffer and stored at −70° C. All protein samples were thawed at room temperature and passed four times over immobilized N-acetylglucosamine (Pierce) micro-affinity columns (Mansfield, M. A., et al., Planta 173, 482–489 (1988)). After extensive washing of the column with TA buffer [50 mM Tris-acetate pH 5.0,and 100 mM NaCl], barley lectin was eluted with 150 ul 100 mM N-acetylglucosamine, and lyophilized. The radiolabeled barley lectin was analyzed by SDS-PAGE on 12.5% polyacrylamide gels and visualized by fluorography as detailed in Mansfield et al. (Mansfield, M. A., et al., Planta 173, 482–489 (1988)).

Tobacco Suspension Culture (NT) Cell and Plant Transformation

The binary vector pGA643 constructs containing wt or ctpp$^-$were mobilized to *Agrobacterium tumefaciens*

LBA4404 as described in Wilkins et al (Wilkins, T. A., et al., Plant Cell 2, 301–313 (1990)). NT suspension cells were co-cultivated with agrobacteria harboring wt and ctpp⁻ pGA643 constructs according to An (An, G., Plant Physiol. 79, 568–570 (1985)) and plated on MS 0.2 mg/L 2,4-D agar supplemented with 500 mg/L carbenicillin and 150 mg/L kanamycin. After 3–4 weeks, calli were transferred to fresh selective media. Transformed calli expressing barley lectin were grown in liquid MS 0.2 mg/L 2,4-D media with 500 mg/L carbenicillin and 150 mg/L kanamycin on a gyratory shaker at 150 rpm at 28° C. The ctpp⁻transformed plants were obtained as described in Wilkins et al (Wilkins, T. A., et al., Plant Cell 2, 301–313(1990)).

RNA Gel Blot Analysis

Total RNA was isolated from untransformed and transgenic tobacco suspension culture cells and plants as described (Nagy, F., et al., Plant Molecular Biology Manual B4, 1–29 (1988). Twenty ug of total RNA from each sample was fractionated on 2% agarose gels containing 6% formaldehyde and blotted onto nitrocellulose. The nitrocellulose blot was hybridized with $^{32}$P random-primer labeled (Feinberg, A. P., et al., Anal. Biochem. 132, 6–13 (1983)) pBlc3 barley lectin cDNA insert (Lerner, D. R., et al., Plant Physiol. 91, 124–129 (1989)) and washed as previously described (Raikhel, N. V., et al., Planta 126, 406–414 (1988)). Blots were air dried and exposed to XAR-5 film (Kodak) using intensifying screens at −70° C. Autoradiograms were analyzed by scanning densitometry with a Beckman DU-64 spectrophotometer (Beckman Instruments).

Radiolabeling of Transgenic Tobacco Suspension-Cultured Cells

For pulse-chase labeling experiments, 0.5 ml NT cells (per well) from 4-day old cultures were incubated in 24 well Falcon tissue culture plates in the presence of 85 uCi $^{35}$S-met/cys (see above). Two wells or a total of 1 ml of the 4-day NT cells were labeled per time point. The cells were incubated at room temperature with gentle shaking on a gyratory shaker at 75 rpm in the dark for 6 hours. After 6 hours, labeled proteins were chased by adding unlabeled methionine and cysteine to a concentration of 5 mM and 2.5 mM per well, respectively. At the appropriate time points, labeled NT cells are pooled in 1.5 ml microfuge tubes and the cells were separated from the media by centrifugation at 2,000×g for 1 minutes at 4° C.

The culture media was transferred to another tube and centrifuged at (16,000×g) for 10 minutes at 4° C. to remove any unpelleted cells and debris. Proteins in the culture media were concentrated as described above and stored at −70° C. The cells were washed once with 500 ul MS 0.2 mg/L 2,4-D, pelleted by centrifugation at 2,000×g for 1 minute at 4° C. Cells were homogenized in 300 ul extraction buffer [50 mM Tris-acetate pH 5.0, 100 mM NaCl, 0.6% triton X-100 and 0.6 mM dithiothreitol]. To break the cells, the cell suspension was chilled slowly in liquid nitrogen and the ice slurry was homogenized using a motor-driven microfuge pestle (Kontes, Vineland, N.J.). The homogenate was centrifuged at (16,000×g) for 10 minutes at 4° C. to remove debris and stored at −70° C. Radiolabeled barley lectin was purified from the crude protein extracts and analyzed as described above.

Radiolabeling of Tobacco Leaf Protoplasts

Protoplasts for labeling were prepared from fully expanded leaves of 4 to 6 week old axenic shoot cultures of W38-wt and W38-ctpp⁻barley lectin transformants. Leaf protoplasts were prepared as described in Wilkins et al (Wilkins, T. A., et al., Plant Cell 2, 301–313 (1990)) with the exception that the enzyme mixture was dissolved in MS medium supplemented with 1.0 mg/l benzyladenine (BA), 0.1 mg/L naphthaleneacetic acid (NAA) and 0.6M mannitol. To remove broken protoplasts and undigested cells, the protoplasts were pelleted at (50×g) for 10 minutes, resuspended in MS medium with 1.0 mg/l BA, 0.1 mg/L NAA and 0.6M sucrose and centrifuged at (350×g) for 10 minutes in Babcock bottles. The bloating band of protoplasts was washed once and diluted in MS medium with 1.0 mg/l BA, 0.1 mg/L NAA and 0.6M mannitol. Viable protoplasts were quantified as described above.

Vacuole Isolation from Labeled Tobacco Leaf Protoplasts

For isolation of vacuoles, 1.2×10$^6$ protoplasts were incubated in a total of 3.0 mls of MS medium with 1.0 mg/l BA, 0.1 mg/L NAA and 0.6M mannitol supplemented with 300 uCi $^{35}$S-met/cys. Protoplasts were incubated in the dark at room temperature with gentle shaking (50 rpm on a gyratory shaker) for 12 hours. Labeled protoplasts (2×10$^5$) were treated as described above (Radiolabeling of Tobacco Leaf Protoplasts) to confirm synthesis of radiolabeled barley lectin. The remaining 1×10$^6$ protoplasts were pooled and collected by centrifugation at (50×g) for 5 minutes at 4° C.

Vacuoles were isolated as described in Ser. No. 406,318 with minor modifications and gently lysed by osmotic shock. Four volumes of 10 mMHepes-KOH, pH 7.2 was added to the vacuole suspension and incubated at 4° C. for 30 minutes. Membranes and unbroken vacuoles were pelleted 30 minutes at (16,000×g) at 4° C. Soluble proteins were concentrated by precipitation with ammonium sulfate at 70% saturation at 4° C. for at least 2 hours. Precipitated proteins were collected by centrifugation for 10 minutes at (16,000×g) at 4° C. The protein pellet was resuspended in 300 ul 10 mM Hepes-KOH pH 7.2. Activity of the vacuole-specific enzyme alpha-mannosidase was assayed as described by Boller and Kende (Boller, T., et al., Plant Physiol. 63, 1123–1132 (1979)). $^{35}$S-labeled barley lectin was purified and analyzed as described above.

RESULTS

Deletion of the Carboxyl-Terminal Propeptide of Barley Lectin

Figure 1:
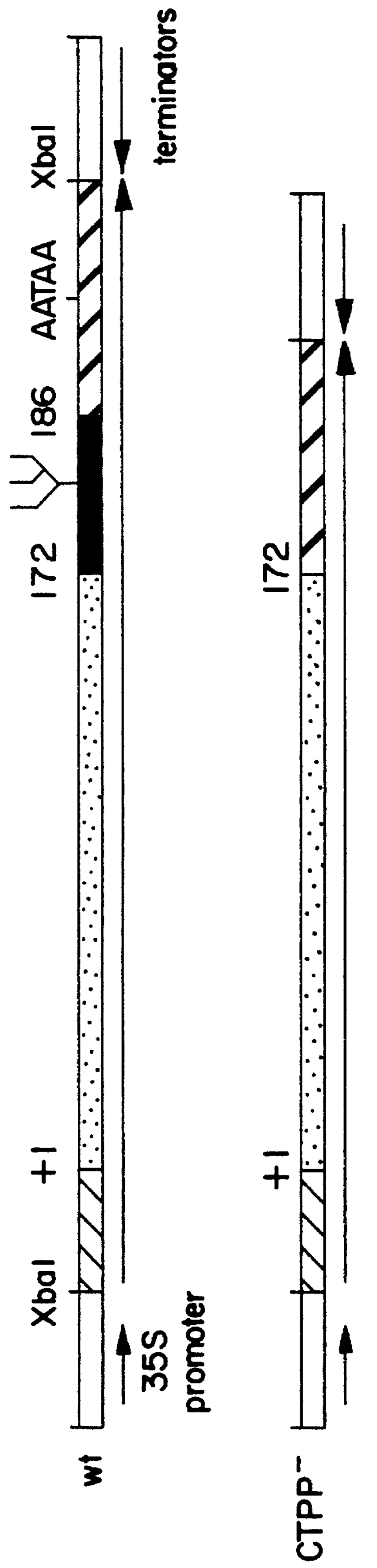
FIG. 1 shows organization of the Wild-Type (WT) and Carboxyl-Terminal Mutant (ctpp$^-$) Barley Lectin cDNAs.

The barley lectin cDNA clone (pBlc3) (Ser. No. 406,318) encodes a polypeptide containing a 26 amino acid signal sequence and a 186 amino acid proprotein. In the lumen of the ER, the signal sequence is cleaved and the polypeptide is co-translationally glycosylated. The proprotein consists of four highly homologous domains of 43 amino acids and a 15 amino acid carboxyl-terminal propeptide (CTPP) which contains an N-linked high mannose glycan. Prior to or concomitant with deposition of mature barley lectin in the vacuole, the glycosylated 15 amino acid CTPP is cleaved to yield the dimer consisting of two identical 18 kD subunits. To investigate the role of the CTPP in the assembly and sorting of barley lectin to vacuoles, a mutant barley lectin cDNA clone lacking the 15 amino acid CTPP was prepared. The CTPP coding region of the cDNA clone pBlc3 (Ser. No. 406,318) was deleted (see Methods) by site-directed mutagenesis (Kunkel, T. A., et al., Methods Enzymol. 154, 367–382 (1987)). A synthetic oligonucleotide complementary to regions flanking the CTPP coding sequence was utilized as a primer to initiate second-strand synthesis of a mutant barley lectin clone lacking the CTPP. The CTPP barley lectin deletion mutant cDNA was subcloned into the binary plant expression vector pGA643 under transcriptional control of the 35S cauliflower mosaic virus promoter (An, G., et al., Plant Molec. Biol. Manual A3, 1–19 (1988)). Constructs containing the CTPP deletion mutant of barley lectin were designated by the code ctpp$^-$(FIG. 1). The pGA643 constructs containing the barley lectin cDNA were designated by the code WT (FIG. 1) (Ser. No. 406,318). Site-directed mutagenesis was used to prepare a ctpp$^-$ barley lectin construct. The wt and ctpp$^-$barley lectin cDNA clones were subcloned into the plant expression vector pGA643 (An, G., et al., Plant Molec. Biol. Manual A3, 1–19 (1988)). Wt barley lectin encodes a polypeptide containing a 26 amino acid signal sequence, followed by a 186 amino acid proprotein (amino acids +1–186). The 15 amino acid CTPP of barley lectin proprotein (amino acids 172–186) contains an N-linked high mannose type glycan as depicted by the branched structure.

Figure 2:
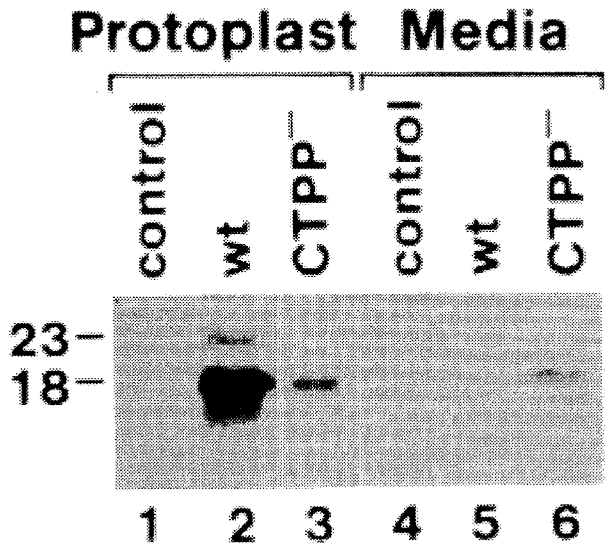
FIG. 2 shows a protein gel blot analysis of transiently expressed WT and ctpp$^-$Barley Lectin cDNA constructs.

Transient Protein Synthesis of Active wt and ctpp$^-$ Barley Lectin in Tobacco Suspension-cultured Cell Protoplasts Barley lectin is localized in vacuoles/protein bodies of embryonic and adult root cap cells of barley (Mishkind, M. L., et al., Science 220, 1290–1292 (1983); and Lerner, D. R., et al., Plant Physiol. 91, 124–129 (1989)). Barley lectin is also correctly processed and targeted to vacuoles in transgenic tobacco cells (Wilkins, T. A., et al., Plant Cell 2, 301–313 (1990)). To determine whether the ctpp$^-$ mutant of barley lectin was synthesized and assembled into an active lectin in tobacco, ctpp$^-$ constructs were transiently expressed in tobacco suspension-cultured cell (NT) protoplasts. Wt and ctpp$^-$ pGA643 constructs were introduced into NT protoplasts via polyethylene glycol treatment (Negrutiu, I., et al., Plant Mol. Biol. 8, 363–373 (1987)) and the protoplasts were pulse-labeled for 12 hours in the presence of a mixture of $^{35}$S-labeled methionine and cysteine ($^{35}$S-met/cys) (see Methods) Protein extracts prepared from the labeled protoplasts and incubation media were fractionated on immobilized GlcNAc. The affinity purified fractions were analyzed under denaturing conditions by SDS-PAGE and fluorography as shown in FIG. 2. Protoplasts from tobacco suspension-cultured cells were transiently transformed with wt and ctpp$^-$pGA643 constructs via direct gene transfer using polyethylene glycol (Negrutiu, I., et al., Plant Mol. Biol. 8, 363–373 (1987)) and were pulse-labeled for 12 hours. Radiolabeled barley lectin was affinity purified from both protoplasts and incubation media and separated by SDS-PAGE as described in Methods. Lanes 2 and 5 represent radiolabeled barley lectin extracted from wt protoplast and corresponding incubation media, respectively. Lanes 3 and 6 are radiolabeled barley lectin from ctpp$^-$ protoplasts and incubation media, respectively. Lanes 1 and 4 refer to extracts prepared from protoplasts treated in the absence of plasmid DNA, and are the negative controls. The sizes of the barley lectin precursor (23 kD) and mature barley lectin (18 kD) are shown on the left. Two polypeptides corresponding to the 23 kD proprotein and 18 kD mature subunit of barley lectin were present in pulse-labeled NT protoplasts expressing the wt construct (lane 2, FIG. 2). Radiolabeled barley lectin was not detected in the incubation media recovered from NT protoplast expressing wt barley lectin (lane 5, FIG. 2). Similarly, barley lectin is not detected in the incubation media of $^{35}$S-met/cys labeled leaf protoplasts from wt transgenic tobacco (Wilkins, T. A., et al., Plant Cell 2, 301–313 (1990)). Only the mature 18 kD subunit of barley lectin was present in the affinity purified extracts from pulse-labeled ctpp$^-$NT protoplasts (lane 3, FIG. 2). Deletion of the carboxyl-terminal propeptide resulted in the appearance of radiolabeled barley lectin in the incubation media of the protoplasts transiently expressing only the ctpp$^-$ construct (lane 6, FIG. 2). These results support the observation (Peumans, W. J., et al., Planta 154, 568–572 (1982)) that the subunits of barley lectin do not require the CTPP to correctly dimerize in vitro. However, the CTPP does appear to be necessary for proper sorting of active barley lectin to the vacuole.

Transformation of wt and ctpp$^-$ Constructs into Tobacco suspension-Cultured Cells and Plants To further investigate the role of the carboxyl-terminal propeptide in the sorting of barley lectin to vacuoles, tobacco plants and suspension-cultured cells were stably transformed with wt and ctpp$^-$ constructs. In our previous experiments, we have analyzed the expression and intracellular localization of barley lectin in transgenic tobacco plants. However, suspension-cultured cells offer many advantages for the analysis of protein sorting. NT cells can be readily transformed at a high frequency by co-cultivation with *Agrobacterium tumefaciens* and resulting kanamycin-resistant transformants analyzed within 7–8 weeks after selection. The individual nature of suspension-cultured cells and their immediate contact with the surrounding media allows for the direct analysis of protein secretion from transformed cells.

NT cells were transformed by co-cultivation with *A. tumefaciens* containing wt or ctpp$^-$ pGA643 constructs according to the method of An, G., Plant Physiol. 79, 568–570 (1985). Kanamycin-resistant calli expressing barley lectin were designated NT-wt and NT ctpp$^-$, respectively. Kanamycin-resistant tobacco plant transformants containing the ctpp$^-$ deletion mutant of barley lectin were generated as described in Ser. No. 406,318. Transgenic plants expressing the mutant barley lectin were designated by the code W38-ctpp$^-$. Tobacco transformants expressing wt barley lectin described in Ser. No. 406,318, were designated by the code W38-wt.

Figure 3:
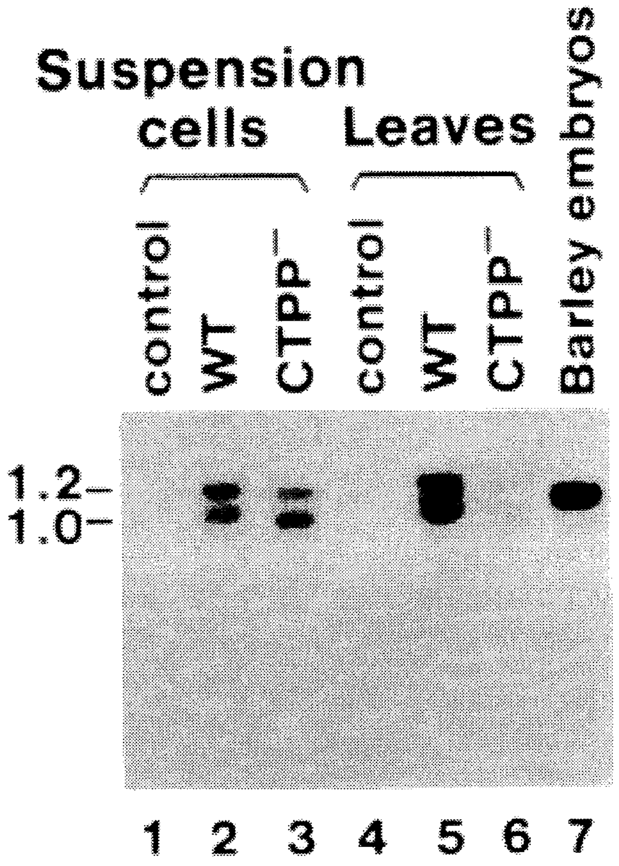
FIG. 3 shows accumulation of steady-state mRNA levels of barley lectin in tobacco suspension-cultured cells (NT) and in transgenic tobacco.

The steady state levels of wt and ctpp$^-$ barley lectin mRNA in transgenic NT cells and tobacco plants were compared by RNA gel blot analysis. Barley lectin mRNA was detected by hybridization with $^{32}$p-labeled Blc3 insert (Lerner, D. R., et al., Plant Physiol. 91, 124–129 (1989)). FIG. 3 depicts the relative levels of barley lectin mRNA in total RNA isolated from wt and ctpp$^-$ transformants. RNA gel blot analysis of total RNA from the tobacco suspension-cultured cells (NT) or tobacco leaves. Total RNA (20 ug) from untransformed NT cells (lane 1), transformed NT cells containing wt (lane 2) or ctpp$^-$ (lane 3) barley lectin cDNA constructs untransformed tobacco (W38) (lane 4), transgenic tobacco plants containing wt (lane 5) or ctpp$^-$ (lane 6) barley lectin cDNA constructs, were separated by electrophoresis analyzed as in FIG. 4. The molecular mass (in kilodaltons) of the wt barley lectin precursor (23 kD) and mature subunit (18 kD) are displayed on the left. Two mRNA species of 1.2 kb and 1.0 kb were observed in total RNA from wt transformants (lanes 2 and 5, FIG. 3). Two slightly smaller mRNA species of 1.15 kb and 1.05 kb were detected in total RNA from ctpp$^-$ transformants (lanes 3 and 6, FIG. 3). hybridization of $^{32}$P-labeled barley lectin cDNA to total RNA from untransformed NT cells and tobacco leaves was detected at high stringency hybridization conditions (lanes 1 and 4, FIG. 3). The relative levels of ctpp$^-$ barley lectinm-RNA were three- to four-fold lower than corresponding wt mRNA in transformants as determined by scanning densitometry (lanes 5 and 6, FIG. 3). This disparity in the relative mRNA levels was also manifested in the steady state accumulation of barley lectin protein in wt and ctpp$^-$ transgenic plants (see below).

The CTPP Mutant of Vacuolar Barley Lectin is Secreted in Transgenic Tobacco Suspension-Cultured Cells and Plants Evidence to date suggests that secretory proteins destined for the vacuoles/lysosomes of plant, mammalian and yeast cells require specific targeting signal(s) for proper sorting (reviewed in Chrispeels, M. J., Ann. Rev. Plant Physiol. Plant Molec. Biol. 42, in press (1991)). Secretory proteins which lack or have altered targeting signals cannot be recognized by the vacuolar protein sorting machinery, will be secreted via the default pathway as a consequence (Rothman, J. E., Cell 50, 521–522 91987); Wieland, F. T., et al., Cell 50, 289–300 (1987); Dorel C., et al., J. Cell Biol. 108, 327–337 (1989); and Denecke, J., et al., Plant Cell 2, 51–59 (1990)).

To examine the processing, assembly, and sorting of barley lectin in tobacco suspension-cultured cells, NT-wt and NT-ctpp$^-$ cells were pulse-labeled for 6 hours in the presence of $^{35}$S-met/cys and chased for an additional 10 hours in the presence of unlabeled methionine and cysteine (met/cys). Crude intracellular and extracellular protein extracts were fractionated on immobilized GlcNAc. Radiolabeled barley lectin was analyzed by SDS-PAGE and fluorography (FIG. 4). The 23 kD polypeptide and mature 18 kD subunits of barley lectin were readily discernible in NT-wt cells (lane 1, FIG. 4A). During the 10 hour chase period, the 23 kD polypeptide became almost undetectable. The disappearance of the precursor was accompanied by a corresponding increase in the level of the intracellular 18 kD mature subunit (lane 2, FIG. 4A). Neither the labeled precursor nor the mature polypeptide of barley lectin were present in the NT-wt incubation media during the 10 hour chase period (lanes 3 and 4, FIG. 4A). However, the 18 kD mature polypeptide of barley lectin was detected in both the NT-ctpp$^-$ cells (lane 1, FIG. 4B) and incubation media (lane 3, FIG. 4B). During the 10 hour chase period, there was a decrease in the level of intracellular 18 kD polypeptide (lane 2, FIG. 4B) and a corresponding increase in the amount of 18 kD barley lectin subunit in the media (lane 4, FIG. 4B). Radiolabeled 18 kD subunit was still present in the NT ctpp$^-$ cells after a 10 hour chase.

To extend the analysis of ctpp$^-$ barley lectin secretion, W38-wt and W38-ctpp$^-$ leaf protoplasts were pulse-labeled for 10 hours in the presence of $^{35}$S-met/cys. Labeled proteins were chased with unlabeled met/cys for an additional 18 hours. Radiolabeled barley lectin was affinity purified from crude protein extracts of protoplasts and incubation media at specific intervals during the chase period (see FIG. 5) and analyzed as described above At the start of the chase (0 hr, FIG. 5A), both the 23 kD proprotein and mature 18 kD subunit were present in wt protoplasts. During the course of the chase, the level of the 23 kD precursor gradually decreased whereas the level of 18 kD mature subunit correspondingly increased. However, some 23 kD precursor was still visible after 18 hours of chase in the wt protoplast (18 hour, FIG. 5A), indicating the continued low level incorporation of labeled amino acids into newly synthesized polypeptides. After 10 hours of pulse-labeling, mature 18 kD polypeptides derived from the CTPP barley lectin mutants accumulated to higher levels in the incubation media than intracellularly (FIG. 5B). Over the course of the chase the level of the intracellular 18 kD subunit decreased and concomitantly increased in the ctpp$^-$ protoplast incubation media (FIG. 5B). After 18 hours of chase, some and 18 kD polypeptides were still associated with the protoplast fraction. The subcellular distribution of the residual 18 kD ctpp$^-$ polypeptide was examined by organelle fractionation as described in Wilkins, T. A., et al., Plant Cell 2, 301–313 (1990). Vacuoles were isolated from labeled W38-wt and W38-ctpp$^-$ protoplast as described in Ser. No. 406,318. The vacuoles were lysed by osmotic shock and the soluble vacuolar proteins were fractionated on immobilized GlcNAc. Affinity purified radiolabeled barley lectin was visualized by SDS-PAGE and fluorography. The 18 kD barley lectin subunit was only discernible in the vacuole preparation from wt protoplasts after 60 hours of exposure and not in vacuoles from ctpp$^-$ transformants (data not shown). However, after a 14 day exposure of the same gel, another band corresponding to the 23 kD precursor was visible in the vacuolar fraction of W38-wt protoplast and an 18 kD polypeptide could be seen in vacuoles isolated from W38-ctpp$^-$ protoplasts (data not shown). The appearance of the 23 kD polypeptide suggests that the wt vacuole preparation is contaminated with ER and Golgi organelles. Therefore, it is difficult to assess whether the presence of radiolabeled barley lectin in the ctpp$^-$ vacuoles is the result of some remaining vacuolar targeting of barley lectin lacking the CTPP or, whether it results from contamination of the vacuole preparation by ER and Golgi compartments. Another possibility is that the chase was incomplete and that some low level incorporation of $^{35}$S-met/cys into newly synthesized barley lectin proprotein still continued.

In this experiment, a low level of the 23 kD proprotein was discernible in the incubation media of W38-wt protoplasts. The absence of any detectable 18 kD subunit in the media indicates that the presence of the glycosylated proprotein is not due to protoplast breakage.

Discussion of Example

The vacuole is a multifunctional organelle important in the regulation and maintenance of plant cell growth and development. Recently, much research has been directed toward understanding the mechanism controlling the sorting and delivery of secretory proteins to vacuoles. To understand the mechanisms involved in protein sorting to vacuoles, it is necessary to identify and characterize the sorting signals from various vacuolar proteins with different functional and structural properties. We have established both transgenic and transient gene expression systems to investigate the mechanisms of post-translational processing and sorting of barley lectin to plant cell vacuoles. In transgenic tobacco, barley lectin is correctly synthesized as a gycosylated proprotein and assembled as an active GlcNAc-binding dimer in the ER (Wilkins, T. A., et al., Plant Cell 2, 301–313 (1990)). The proprotein is transported through the Golgi apparatus and is processed to its mature form by removal of a glycosylated 15 amino acid CTPP before or concomitant with deposition of the mature protein in the vacuoles of tobacco leaves (Wilkins, T. A., et al., Plant Cell 2, 301–313 (1990)). The rate of processing of the precursor is regarded by the presence of an N-linked high mannose glycan on the CTPP. However, the glycan is not required for vacuolar targeting of barley lectin (Wilkins, T. A., et al., Plant Cell 2, 301–313 (1990)).

Barley lectin and wheat germ agglutin (WGA) are presumed to share a conserved molecular structure (Wilkins, T. A., et al., Plant Cell 2, 301–313 (1990)). Extensive X-ray crystallographic and sequence analysis of mature WGA has revealed that identical 18 kD subunits are composed of four highly homologous domains, each of which consists of a tightly folded core stabilized by four disulfide bonds (Wright, C. S., J. Mol. Biol. 194, 501–529 (1987)). Examination of the WGA crystal structure does not reveal any region(s) which extend from the surface of the molecule. The lectins from barley, wheat and rice are all initially synthesized as high molecular weight proproteins with glycosylated CTPPs (Raikhel, N. V., et al., Proc. Natl. Acad. Sci. U.S. 84, 6745–6749 (1987); Mansfield, M. A., et al., Planta 173, 482–489 (1988); Lerner, D. R., et al., Plant Physiol. 91, 124–129 (1989); and Wilkins, T. A., et al., Plant cell 1, 541–549 (1989)). These CTPPs (FIG. 6) are predicted by computer analysis of protein secondary structure to form amphipathic alpha-helices (Wilkins, T. A., et al., Plant Cell 1, 541–549 (1989)). With the exception of the WGA isolectins and barley lectin, the primary amino acid sequences of the carboxyl-terminal propeptides of the Gramineae lectins (Raikhel, N. V., et al., Proc. Natl. Acad. Sci. U.S. 84, 6745–6749 (1987); Lerner, D. R., et al., Plant Physiol. 91, 124–129 (1989); Wilkins, T. A., et al., Plant Cell 1, 541–549 (1989); and Smith, J. et al., Plant Mol. Biology 180 601–603 (1989)) and the intracellular isoforms of *N. tabacum* (Shinshi, H., et al., Proc. Natl. Acad. Sci. U.S.A. 85, 5541–5545 (1988)) and *N. plumbaginifolia* (DeLoose, M., et al., Gene 70, 13–23 (1988)) beta-1,3-glucanase are not conserved. The stars above the residues denote the utilized N-linked glycosylation sites. Acidic residues (E=glutamic acid, D=Aspartic acid) are underlined. In contrast to tightly folded and compact lectin domains, the CTPP may be more exposed on the surface of the lectin dimer and free to interact with other proteins or protein complexes. Based on examination of the compact WGA crystal structure and predicted conformation of the precursor CTPP, we have hypothesized that the CTPP may function as a sorting determinant for targeting of barley lectin to the vacuole.

To examine the role of the carboxyl-terminal propeptide in vacuolar sorting of barley lectin, we have expressed a CTPP deletion mutant of barley lectin in tobacco protoplasts, transgenic suspension-cultured cells and transgenic plants. Using these three different systems, deletion of the barley lectin CTPP resulted in the secretion of the mature GlcNAc-binding protein. Low levels of radiolabeled barley lectin were still detected intracellularly after 18 hours of chase with unlabeled met/cys. We have not established whether the remaining intracellular barley lectin was sorted to the vacuole without a CTPP or whether it remains sequestered within the secretory pathway. It has previously been demonstrated that deletion of the propeptide region containing the sorting determinant of the yeast vacuolar proteinase A, still resulted in some small fraction of the protein being transported to the vacuole (Klionsky, D. J., et al., Mol. Cell Biol. 8, 2105–2116 (1988)). It is clear however, that barley lectin is missorted if it is synthesized without the CTPP and the data strongly suggests that the carboxyl-terminal propeptide is necessary for efficient sorting of barley lectin to vacuoles.

Many vacuolar proteins are synthesized as larger precursors and are processed to their mature form prior to or upon arrival of the proprotein to vacuoles. Similar to the Graineae lectins, the vacuolar isoforms of beta-1,3-glucanases of *Nicotiana tabacum* and *N. plumbaginifolia* are initially synthesized as glycosylated precursors and processed into their mature forms by the removal of a glycosylated carboxyl-terminal propeptide (Shinshi, H., et al., Proc. Natl. Acad. Sci. U.S. 85, 5541–5545 (1988)); and Van Den Bulcke, M., et al., Proc. Natl. Acad. Sci. U.S.A. 86, 2673–2677 (1989)). By analogy to the barley lectin CTPP, the beta-1,3-glucanase CTPPs may be necessary for vacuolar sorting. The primary amino acid sequences of the Gramineae lectin and the tobacco beta-1,3-glucanase CTPPs are not conserved (FIG. 6), however, these CTPPs all contain a utilized N-linked glycosylation site and have an overall negative charge due to acidic amino acids. Features such as the acidic nature of these glycopeptides and/or secondary structure may be important in the molecular mechanisms of vacuolar sorting for these proteins.

Interestingly, in contrast to the Gramineae lectins, distinct extracellular isoforms of the beta-1,3-glucanases have been identified in *N. plumbaginifolia* (Van Den Bulcke, M., et al., Proc. Natl. Acad. Sci. U.S. 86, 2673–2677 (1989)). It is not shown whether the extracellular forms have been synthesized with a CTPP and then processed to the intracellular forms. Recently, another beta-1,3-glucanase cDNA clone was isolated from *N. tabacum* (Neale, A. D., et al., Plant Cell, 2, 673–684 (1990)) was isolated. This clone is homologous to the vacuolar beta-1,3-glucanase cDNA isolated by Shinshi et al. (Shinshi, H., et al., Proc. Natl. Acad. Sci. U.S. 85, 5541–5545 (1988)), however, it lacks the region encoding the CTPP (Neale, A. D., et al., Plant Cell, 2, 673–684 (1990)).

Mechanisms of Barley Lectin Sorting

In mammalian cells, sorting of lysosomal enzymes tagged by mannose-6-phosphate interact with the mannose-6-phosphate receptor system in the trans-Golgi and are segregated into vesicles destined for the lysosome (Kornfeld, S., et al., Ann. Rev. Cell Biol. 5, 483–525 (1989)). Likewise in yeast, the soluble vacuolar protein CPY is believed to be sorted in a late Golgi compartment (Valls, L. A., et al., Cell 48 887–897 (1987)). Studies with the inhibitor monensin on the processing of barley lectin also suggest that sorting of the lectin precursor is a late Golgi event (Wilkins, T. A., et al., Plant Cell 2, 301–313 (1990)). Monensin primarily disrupts protein transport and sorting in the trans-Golgi (Tartakoff, A. M., Cell 32, 1026–1028 (1983)); and Chrispeels, M. J., Planta 158, 140–151 (1983)). In the presence of monensin, cleavage of the CTPP and transport of the barley lectin precursor from the Golgi is blocked (Wilkins, T. A., et al., Plant Cell 2, 301–313 (1990)). The sorting apparatus for the barley lectin precursor is therefore presumably associated with the trans-Golgi compartment. In this paper, we have demonstrated that the CTPP is necessary for sorting of barley lectin proproteins to plant vacuoles. By analogy with the receptor-mediated lysosomal protein sorting system, the CTPP is recognized by a sorting system and that the proprotein is segregated into vesicles destined for the vacuoles in the trans-Golgi network (FIG. 7). The schematic representation of one subunit of a barley lectin dimer was adapted from crystal structure of WGA (Wright, C. S., J. Mol. Biol. 194, 501–529 (1987)). Each of the four highly homologous domains of barley lectin is represented by a circle. The glycosylated carboxyl-terminal propeptide is depicted as a spiral to denote the predicted amphipatic alpha-helical structure of the peptide and the structure of the N-linked high mannose type glycan was adapted from Montreuil (Montreuil, J., Biol. Cell 51, 115–131 (1984)). The carboxylterminal propeptide of barley lectin is necessary for sorting of this protein to vacuoles. The barley lectin mutant lacking this sorting signal is secreted. The final step in the maturation of barley lectin has not been precisely characterized It remains unknown whether the carboxyl-terminal propeptide is cleaved from the precursor while enroute to or after deposition of the mature lectin in the vacuoles. The N-linked high mannose glycan present on the proprotein CTPP shows the rate of processing of the proprotein, possibly by masking the availability of the CTPP for processing (Wilkins, T. A., et al., Plant Cell 2, 301–313 (1990)). However, the glycan is not required for sorting of barley lectin to vacuoles (Wilkins, T. A., et al., Plant Cell 2, 301–313 (1990)). It has been suggested that the function of some glycans may be to mask "accidental" targeting signals (Tague, B. W., et al., Plant Cell 2, 533–546 (1990)). Deglycosylation of the carboxyl-terminal glycopeptide may be required for recognition of the CTPP by the sorting machinery and the subsequent processing of the proprotein. This invokes a model whereby the glycosylated proprotein is processed to the mature lectin by a two step procedure (see Wilkins, T. A., et al., Plant Cell 2, 301–313 (1990)). An intermediate processing form of barley lectin containing a deglycosylated CTPP has not yet been identified, suggesting that he next processing step, the removal of the CTP, is very fast, or processing of the gycosylated CTPP actually occurs in a single step. The later model suggests that glycosylation of the CTPP does not affect its recognition as a sorting determinant.

Proteins lacking or failing to present an appropriate sorting determinant to the sorting apparatus would be secreted by default from the Golgi via secretory vesicles. For example, the ctpp$^-$ barley lectin mutant lacking the sorting signal was secreted (FIG. 7). Similarly, overproduction of a vacuolar protein may saturate the sorting pathway, thereby resulting in the secretion of the protein via the default pathway as has been hypothesized by Stevens et al (Stevens, T. H., et al., J. Cell Biol. 102, 1551–1557 (1986)). Secretion of barley lectin in W38-wt protoplasts to the incubation media presumably resulted from the overproduction of the 23 kD glycosylated proprotein. Overproduction of the proprotein may have saturated either the system which deglycosylates the proprotein or the sorting apparatus which recognizes the CTPP and targets barley lectin to plant vacuoles.

EXAMPLE 2

It has been previously shown in Example 1 that the 15 amino acid carboxyl-terminal propeptide of probarley lectin is necessary for the proper sorting of this protein to the plant vacuole. A mutant form of the protein lacking the carboxyl-terminal propeptide is secreted. To test whether the carboxyl-terminal propeptide is the vacuole sorting determinant of probarley lectin, the processing and sorting of a series of fusion proteins, containing the secreted protein, cucumber chitinase and regions of probarley lectin, in transgenic tobacco were examined. Pulse-labeling experiments demonstrated that the fusion proteins were properly translocated through the tobacco secretory system and that cucumber chitinase and cucumber chitinase fusion proteins lacking the carboxyl-terminal propeptide were secreted. The cucumber chitinase fusion protein containing the carboxyl-terminal propeptide was properly processed and sorted to the vacuole in transgenic tobacco as confirmed by organelle fractionation and electron microscopy immunocytochemistry. Therefore, the barley lectin carboxy-terminal propeptide is both necessary and sufficient for protein sorting to the vacuole in transgenic plants.

Methods

All standard recombinant DNA procedures used in this study were carried out as described in Sambrook, et al (Sambrook, J., et al., Molecular Cloning: A Laboratory Manual, 2nd ed. (Cold Spring Harbor, N.Y.: Cold Spring Harbor Laboratory) (1990)), unless otherwise noted. DNA restriction and modifying enzymes were obtained from New England BioLabs (Beverly, Mass.). All other reagents, unless specified were purchased from Sigma.

Construction of Cuc Chit Gene Fusions pSCU1 (kindly provided by J. M. Neuhaus and T. Boller, Friedrich Miescher Institute, Basel Switzerland) contained a cucumber chitinase gene (Metraux, J. P., et al., Proc. Natl. Acad. Sci. U.S.A. 86, 896–900 (1989)) in which the putative Cuc Chit signal sequence coding region (amino acids 1 to 26) had been replaced with the signal peptide DNA sequence from the basic tobacco chitinase (amino acids 1 to 26) (Shinshi, H., et al., Plant Mol. Biol. 14, 357–368 (1990); and Shinshi, H., et al, Proc. Natl. Acad. Sci. U.S. 84, 89–93 (1987)). The restriction fragment containing the Cuc Chit insert from pSCU1 was subcloned into pUCl18 (Viera, J., and J. Messing, Methods Enzymol. 153, 3–11 (1987)). SalI and XbaI restriction sites were inserted in the 5' untranslated region of Cuc Chit by site-directed mutagenesis (Kunkel, T. A., et al., Methods Enzymol. 154, 367–382 (1987)). An additional XhoI site was created by site-directed mutagenesis preceding the codon for $Gly^{289}$ of the Cuc Chit deduced amino acid sequence (Metraux, J. P., et al., Proc. Natl. Acad. Sci. U.S. 86, 896–900 (1989)). This construct will be called Cuc Chit (FIG. 1, B1).

Two separate oligonucleotides were used to insert XhoI restriction sites by site-directed mutagenesis into the BL cDNA (Lerner, D. R., and N. V. Raikhel, Plant Physiol. 91, 124–129 (1989)) in pUC118 (Wilkins, T. A., et al., Plant Cell 2, 301–313 (1990)). Three BL cDNA mutants were constructed containing the following XhoI site(s): (1) BL1 had a single XhoI site that preceded the codon for $Gln^{27}$ the first amino acid of the mature 18-kD subunit of BL; (2) BL2 had a single XhoI site that preceded the codon for $gly^{197}$; (3) BL3 was a double BL cDNA mutant containing both XhoI sites presented in BL1 and BL2.

The Cuc Chit gene fusions were constructed as follows: Cuc Chit-proBL was constructed by cloning an SalI-XhoI restriction fragment containing the Cuc Chit coding region into the SalI-XhoI restriction sites of BL1 in pUCllS; Cuc Chit-BL was constructed by cloning the XhoI restriction fragment from BL3 into the XhoI restriction site of Cuc Chit; Cuc Chit-CTPP was constructed by cloning the SalI-XhoI restriction fragment of Cuc Chit into the SalI-XhoI restriction sites of BL2. The Cuc Chit-CTPP[Gly$^-$] gene fusion was constructed by altering the CTPP N-linked glycosylation site within the Cuc Chit-CTPP gene fusion as described previously (Wilkins, T. A., et al., Plant Cell 2, 301–313 (1990)). All mutations and constructs were checked and confirmed by $^{35}S$ dideoxy sequencing (Sanger, F., et al., Proc. Natl. Acad. Sci. U.S. 56, 5463–5467 (1977)). XbaI restriction fragments containing Cuc Chit and Cuc Chit gene fusions were subcloned into the XbaI site of the plant expression vector pGA643 (An, G., et al., Plant Mol. Biol. Manual A3, 1–19 (1988)).

Transient Gene Expression in Tobacco Suspension Protoplasts

Cuc Chit and Cuc Chit gene fusions were introduced into tobacco protoplasts as described previously (Bednarek, S. Y., et al., Plant Cell 2, 1145–1155 (1990)), with the exception that the transiently transformed protoplasts were resuspended to a final density of $2.5\times10^5$ protoplasts per ml in 1.0 ml of liquid Murashige and Skoog (MS) medium (Murashige, T., and F. Skoog, Physiol. Plant. 15, 473–497 (1962)) supplemented with 0.2 mg/L 2,4-D and 0.4M betaine monohydrate.

To examine expression, transformed protoplasts were incubated for 14 hours in the dark at room temperature with gentle shaking in the presence of 100 μCi $^{35}$S protein labeling mixture ($^{35}$S-Met/Cys)(specific activity 1000 Ci/mmol to 1100 Ci/mmol)(DuPont-New England Nuclear Research Products, Boston Mass.). Labeled proteins were chased for an additional 10 hours with an excess of unlabeled met and cys (final concentration of 15 mM and 7.5 mM, respectively). Protoplasts and incubation media were transferred to 1.5 ml microfuge tubes and separated by brief centrifugation (15–20 sec) at 800 g. The protoplast pellets were lysed in 500 μl of TNET 250 (25 mM Tris-HCl, pH 7.5, 250 mM NaCl, 5 mM EDT, 1% Triton X-100 [v/v]) (Firestone, G. L., and S. D. Winguth, Methods Enzymol. 182, 688–700 (1990)) and cleared of insoluble debris by centrifugation at 16,000 g for 5 minutes at 4° C. The extracellular protein fraction was prepared from the filtered incubation media as described in Bednarek et al. (Bednarek, S. Y., et al., Plant Cell 2, 1145–1155 (1990)) with the exception that 50 mg BS was added as nonspecific "carrier" protein. The culture medium/BSA protein precipitates were resuspended in 500 μl TNET250. For immunoprecipitation, 100 μl of 50 mg/ml BS was added to the protoplast and media extracts.

Plant Transformation

Tobacco plants (*Nicotiana tabacum* cv Wisconsin 38) were transformed with pGA643 Cuc Chit and Cuc Chit gene fusions as described in Wilkins et al (Wilkins, T. A., et al., Plant Cell 2, 301–313 (1990)). Axenic shoot cultures of transformed tobacco were maintained and propagated by node cuttings on solid MS medium without exogenous hormones.

Isolation and Radiolabeling of Transformed Tobacco Leaf Protoplasts

Protoplasts were prepared and isolated as described previously (Bednarek, S. Y., et al., Plant Cell 2, 1145–1155 (1990)), with the exception that the cellulase/macerozyme mixture was prepared in MS medium supplemented with 0.1 mg/L naphthaleneacetic acid, 1.0 mg/L benzyladenine, and 0.6M betaine monohydrate (MS 0.1/1.0, 0.6M betaine). Protoplasts were purified by flotation in MS 0.1/1.0 medium supplemented with 0.6M sucrose, washed once, and diluted to a final concentration of 400,000 protoplasts per milliliter in MS 0.1/1.0, 0.6M betaine. Viable protoplasts were quantified (Bednarek, S. Y., et al., Plant Cell 2, 1145–1155 (1990)) and labeled as described in Wilkins et al (Wilkins, T. A., et al., Plant Cell 2, 301–313 (1990)) with $^{35}$S Met/Cys. Extracts of intracellular and extracellular proteins were prepared for immunoprecipitation as described above.

Vacuole Isolation

Protoplasts for vacuole isolation were prepared as described above. Vacuoles were released from the protoplasts by a combination of osmotic and thermal shock. Viable protoplasts ($1\times10^7$) were chilled on ice for 30 minutes and then pelleted at 50 g for 10 minutes at 4° C. Protoplast were gently lysed in lysis buffer (0.2M sorbitol, 10% [w/v] Vicoll 400, 10 mM Hepes-KOH, pH 7.5, 10 μg/ml neutral red) and preheated to 45° C. Vacuoles were purified by flotation on a discontinuous Ficoll density gradient. The protoplast lysate was overlaid with two steps containing 5% [w/v] Ficoll 400 in 0.6M betaine, 10 mM Hepes-KOH, pH 7.5, and 0.6M betaine, 10 mM Hepes-KOH, pH 7.5; the gradients were centrifuged in a swinging bucket rotor at 5000 g for 30 minutes at 4° C. Vacuoles were recovered from the 0%/5% (w/v) Ficoll 400 interface, quantitated using a hemocytometer, and gently lysed by osmotic shock. The vacuole suspension was diluted with 5 volumes of 10 mM Hepes-KOH, pH 7.5, and incubated at room temperature for 10 minutes. Membranes and unbroken vacuoles were cleared from the lysate by centrifugation at 100,000 g for 30 minutes at 4° C. Soluble proteins were concentrated by ammonium sulfate (70% saturated at 20° C.) and resuspended in 10 mM Hepes-KOH, pH 7.5, 0.5% (v/v) Triton X-100. For subcellular marker enzyme assays, extracts representing total protoplast proteins were prepared. Protoplasts were lysed in 10 mM Hepes-KOH, pH 7.5, 0.5% (v/v) Triton X-100 and cleared of insoluble material by centrifugation at 16,000 g for 10 minutes at 4° C.

For immunoblot analysis, equal amounts of crude vacuole and protoplast lysate, relative to α-mannosidase activity, were precipitated with ice cold acetone (70% final concentration) for 1 hour at −20° C. and collected by centrifugation at 16,000 g at 4° C. Samples were resuspended in 30 μl SDS-PAGE sample buffer (50 mM Tris-HCl, pH 6.8, 2% [w/v] SDS, 1.0% [v/v] β-mercaptoethanol, 10% [v/v] glycerol, 0.01% [w/v] bromophenol blue), heated at 95° C. for 5 minutes, and run on a 12.5% SDS-polyacrylamide gel. Gels were electroblotted onto Immobilon-P Membrane (Millipore Corp., Bedford, Mass.) (Towbin, H., et al., Proc. Natl. Acad. Sci. U.S. 76, 4350–4354 (1979)), and the membranes were blocked for 2 hours with TBS (20 mM Tris-HCl, pH 7.4, 150 mM NaCl) containing 3% (w/v) gelatin and 1% (w/v) BSA. The membranes were incubated for 1.5 hours with anti-Cuc Chit antiserum diluted 1:1250 in TBS containing 1% (w/v) BS and 0.05% (v/v) Tween-20. After washing in TBS-0.1% (v/v) Tween-20, membranes were incubated for 1 hour with goat anti-rabbit antibody conjugated to alkaline phosphatase (Kirkegaard and Perry Lab Inc., Gaithersburg, Mass.) diluted 1:5000 in TBS containing 1.0; % (w/v) BSA and 0.5% (v/v) Tween-20. Secondary antibody binding was visualized as described by Blake et al (Blake, M. S., et al., Anal. Biochem. 136 175–179 (1984)).

Marker Enzyme Assays

NADH-cytochrome-c reductase was assayed by the method of Lord (Lord, J. M., Endoplasmic reticulum and ribosomes. In Isolation of membranes and organelles from plant cells, J. L. Hall and A. L. Moore, eds (New York: Academic Press), pp. 119–134 (1983)) with minor modifications. The assay (0.5 ml final volume) contained 20 mM potassium-phosphate buffer, pH 7.2, 0.5 mM NADH, 50 μM oxidized cytochrome c, 0.5% (v/v) Triton X-100. The NADH dependent reduction of cytochrome c was followed at 550 nm in a Beckman DU54 spectrophotometer (Beckman Instruments, Fullerton Calif.) at room temperature. The effects of 1 mM KCN and 1 μM antimycin on enzyme activity were investigated. Glucose-6-phosphate dehydrogenase was assayed as described by Simcox et al (Simcox, P. D., et al., L. Plant Physiol. 59, 1128–1132 (1977)). α-Mannosidase was assayed as described by Boller and Kende (Boller, T., and H. Kende, Plant Physiol. 63, 1123–1132 (1979)).

Immunoprecipitation and Analysis of Immunoprecipitated Proteins

Cuc Chit and Cuc Chit fusion proteins were purified by immunoprecipitation. To remove nonspecifically binding proteins, $^{35}$S-labeled protoplast and media extracts were treated with 25 μl of nonimmune rabbit sera for 30 minutes at room temperature. Nonspecific protein immunocomplexes were reacted with fixed *Staphylococcus aureus* for 30 minutes at room temperature and removed by centrifugation at 16,000 g for 5 minutes. Two microliters of anti-Cuc Chit antiserum was added to the cleared extracts and incubated at room temperature for 15 minutes. Immunocomplexes were collected on protein A-Sepharose CL-4B beads (Pharmacia, Piscataway, N.J.) for 15 minutes at room temperature and washed three times with TNET 250. To further reduce nonspecific background, immunocomplexes were released from the protein A-Sepharose CL-4B beads by detergent solubilization with 1.0% SDS as described previously (Firestone, G. L., and S. D. Winguth, Methods Enzymol. 182 688–700 (1990)). The solubilized fraction was diluted in 1200 μl of TNET250 buffer with 0.5 mg BSA, and 0.6 μl anti-Cuc Chit antiserum and incubated at room temperature for 15 minutes with continuous mixing. Immunocomplexes were collected on protein A-Sepharose CL-4B beads washed once with TNET250 and once in nondetergent washing buffer (10 mM Tris-HCL pnnH 7.5, 5 mM EDTA). Bound proteins were released by heating at 95° C. for 5 minutes in 30 μl of SDS-PAGE sample buffer. Samples were analyzed by SDS-PAGE on 12.5% polyacrylamide gels (either 3-cm or 9-cm running gels) and visualized by fluorography as described previously (Mansfield, M. A., et al., Planta 173, 482–489 (1988)).

Immunocytochemistry

All procedures were carried out at room temperature. Small pieces of leaf tissues from transgenic tobacco plants were fixed in the mixture of 2% paraformaldehyde and 2.5% glutaraldehyde in 10 mM sodium-phosphate buffer (pnnnH 7.2) with 0.1M sucrose and vacuum infiltrated for 2 hours. After fixation the tissue was washed in the same buffer with 0.5M sucrose three times, 10 minutes each. The tissue was postfixed in 1% $OsO_4$ in the same buffer with 0.05M sucrose for 1 hour and then rinsed in distilled water three times, 5 minutes each. Following dehydration in an ethanol series, the tissue was embedded in London Resin White acrylic resin (Polysciences, Warrington Pa.) and polymerized at 60° C. under vacuum overnight. Thin sections were prepared on an Ultracut E microtome (Reichert-Jung, Vienna Austria) and mounted on formvar-coated nickel grids (Polysciences, Warrington Pa.). Immunocytochemistry was performed essentially as described by Herman and Melroy (Herman, E. M., et al., Plant Mol. Biol. Manual B13, 1–24 (1990)). The primary antibody (rabbit anti-chitinase antiserum) was diluted 1 to 20, and control sections were incubated with nonimmune serum diluted similarly. Protein A-colloidal gold (EY Lab Inc., San Mateo Calif.) was diluted 1 to 50. Thin sections were examined on a JEOL 100CXII transmission microscope (Tokyo, Japan). RESULTS Assembly of Cucumber Chitinase Gene Fusions BL is a 36-kD homodimeric protein, which is localized in the vacuoles/protein bodies of embryonic and root cap cells of barley (Mishkind, M. L., et al., Science 220, 1290–1292 (1983); and Lerner, D. R., and N. V. Raikhel, Plant Physiol. 91, 124–129 (1989)). As shown in FIG. 1A, each BL subunit is initially synthesized as a preproprotein composed of a 2.5-kD signal peptide, an 18-kD polypeptide, and a 1.5-kD CTPP. Within the ER, the proprotein is modified by the covalent addition of a high-mannose-type glycan to the CTPP, to form a 23-kD polypeptide, and dimerizes to form an active N-acetylglucosamine binding protein. During transport to or concomitant with deposition of the protein in the vacuole, the glycosylated CTPPs are cleaved to yield the dimer consisting of two 18-kD subunits.

It has previously been demonstrated that BL is correctly processed and targeted in transgenic tobacco cells (Wilkins, T. A., et al., Plant Cell 2, 301–313 (1990)). Deletion of the 15 amino acid CTPP resulted in secretion of BL indicating that the CTPP is necessary for the proper sorting of this protein to the vacuoles of plant cells (Bednarek, S. Y., et al., Plant Cell 2, 1145–1155 (1990)). To examine whether the CTPP is necessary and sufficient to redirect a reporter protein to plant vacuoles, a chimeric gene containing the cDNA encoding cucumber chitinase (Cuc Chit) (Metraux, J. P., et al., Proc. Natl. Acad. Sci. U.S. 86 896–900 (1989)) was fused with the region of the BL cDNA encoding the CTPP (Lerner, D. R. and N. V. Raikhel, Plant Physiol. 91, 124–129 (1987)) (FIG. 1, B4). In addition, two gene fusions were constructed to determine whether there are any additional topogenic signals within the mature barley lectin 18 kD polypeptide sequence necessary for vacuolar protein sorting (FIG. 8, B2, and B3).

Cuc Chit is a protease-resistant 28-kD protein that is secreted into the intercellular space of cucumber plant in response to viral or pathogen infection (Metraux, J. P., et al., Proc. Natl. Acad. Sci. U.S. 86 896–900 (1989)). No significant homology is found in a comparison of the DNA and deduced amino acid sequences of Cuc Chit and the intracellular basic chitinase isoforms from tobacco and bean (Metraux, J. P., et al., Proc. Natl. Acad. Sci. U.S. 86, 896–900 (1989)). In addition, polyclonal anti-Cuc Chit antisera does not cross react with the chitinases from tobacco (J. Ryals, personal communication). Endonuclease restriction sites were introduced by site-directed mutagenesis (see Methods) into cDNA genes encoding Cuc Chit and proBL to facilitate subcloning of proBL restriction fragments onto the 3' end of the cuc Chit open reading frame. FIG. 1B, is a schematic representation of the proteins encoded by the proBL/CucChit restriction fragment gene fusions. Three Cuc Chit gene fusions were constructed containing the following sequences: (1) the region encoding the barley lectin proprotein (FIG. 8, B2), (2) the region encoding only the mature 18-kD subunit (FIG. 8, B3), and (3) the CTPP coding region (FIG. 8, B4). Although it has been demonstrated that the last carboxyl-terminal amino acid of the mature lectin subunit is a glycine residue ($Gly^{171}$) (Wright, C. S., et al., Biochemistry 23, 280–287 (1984)), the exact site within proBL at which the CTPP is cleaved has yet to be defined. For this reason, we have engineered the 3' end of the Cuc Chit open reading frame to mimic the last two carboxylterminal amino acids of the mature 18-kD barley lectin subunit. The Cuc Chit-CTPP fusion gene was assembled (see Methods) such that the carboxyl-terminal amino acids of Cuc Chit preceding the CTPP, were an acidic amino acid (Glu) followed by a glycine residue.

Cuc Chit gene fusions were subcloned into the plant expression vector pGA643 (An, G., et al., Plant Mol. Biol. Manual A3, 1–19 (1988)) under transcriptional control of the cauliflower mosaic virus 35S promoter. The resulting constructs were transiently expressed in tobacco suspension-cell protoplasts or stably transformed as described (Wilkins, T. A., et al., Plant Cell 2, 301–313 (1990); Bednarek, S. Y., et al., Plant Cell 2, 1145–1155 (1990)) into tobacco cells and plants via Agrobacterium.

Analysis of Cuc Chit Gene Fusions in Transformed Tobacco Cells

To facilitate a rapid analysis of the proBL/Cuc Chit fusion proteins, Cuc Chit/pGA643 constructs were introduced into tobacco suspension-cell protoplasts by polyethylene glycol mediated DNA uptake (Bednarek, S. Y., et al., Plant Cell 2, 1145–1155 (1990)), and the protoplasts were labeled in the presence of a mixture of $^{35}S$-labeled methionine and cysteine ($^{35}S$-Met/Cys) for 14 hours. Cuc Chit and Cuc Chit fusion proteins were purified from protein extracts of the radiolabeled protoplasts and incubation media by immunoprecipitation with polyclonal antisera directed against Cuc Chit and analyzed by SDS-PAGE and fluorography. As shown in FIG. 9, Cuc Chit and Cuc Chit-BL were synthesized as single polypeptides of $M_r$ 28,000 and $M_r$ 26,000, respectively, and secreted from the protoplasts into the incubation media (FIG. 2, lanes 1, 2), indicating that these proteins were properly translocated into the tobacco secretory system and secreted. The labeled polypeptide with an $M_r$ of 46,000 was completely secreted from the tobacco protoplast during a 10 hour chase with unlabeled methionine and cysteine (Met/Cys) and accumulated in the media (data not shown). In tobacco protoplasts transformed with Cuc Chit-proBL, two polypeptides of $M_r$ 51,000 (FIG. 1, B2) and $M_r$ 46,000 were detected intracellularly (FIG. 2, lane 3). These results imply that the Cuc Chit-proBL fusion protein was modified by glycosylation ($M_r$ 51,000) and subsequently processed by removal of the glycopropeptide to the polypeptide with an $M_r$ of 46,000. Likewise, in tobacco protoplasts transformed with Cuc Chit-CTPP, two polypeptides of $M_r$ 33,000 (corresponding to the predicted molecular mass of glycosylated Cuc Chit-CTPP) and M28,000 were detected intracellularly (FIG. 9, lane 4). The presence of the intracellular polypeptide with an $M_r$ of 28,000 suggests that Cuc Chit-CTPP was properly sorted and processed in tobacco cells. In addition, a single polypeptide ($M_r$ 33,000) corresponding to Cuc Chit-CTPP proprotein was detected in the incubation media of tobacco protoplasts transformed with Cuc Chit-CTPP (FIG. 9, lane 4). A very low level of a protein ($M_r$ 51,000) was secreted from tobacco protoplasts expressing Cuc Chit-proBL. The secreted radiolabeled polypeptide with an $M_r$ of 51,000 was discernible only after a very long exposure (>4 weeks) of the fluorogram shown in FIG. 9, (data not shown).

The levels of processed and secreted Cuc Chit-proBL and Cuc Chit-CTPP fusion proteins were compared by densitometric analysis of the fluorogram in FIG. 9. The majority of the Cuc Chit-proBL and Cuc Chit-CTPP fusion proteins (approximately 95% and 75% respectively), were processed and retained intracellularly.

Figures 10A, 10B:
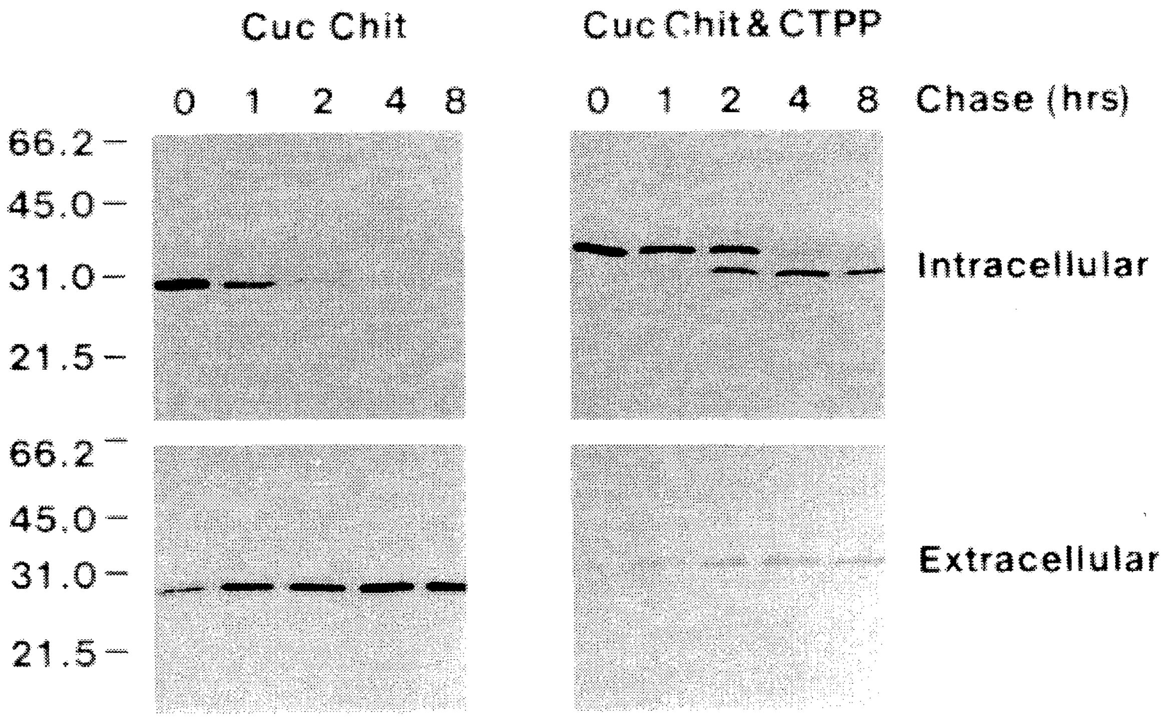

To further analyze the synthesis and processing of Cuc Chit fusion proteins, protoplasts from stably transformed Cuc Chit and Cuc Chit-CTPP transgenic tobacco plants were pulse-labeled for 2.5 hr with $^{35}S$-Met/Cys. Labeled proteins were chased with Met/Cys for an additional 8 hours. Intracellular and extracellular proteins were purified by immunoprecipitation with anti-Cuc Chit antisera and analyzed by SDS-PAGE and fluorography as shown in FIG. 10. As expected for a secreted protein, the level of Cuc Chit ($M_r$ 28,000) decreased intracellularly and correspondingly increased in the incubation media over the course of the chase (FIG. 10A). At the start of the chase a polypeptide with a $M_r$ of 33,000 was detected in Cuc Chit-CTPP protoplasts and at a low level in the incubation media (FIG. 10B, 0 hour). During the 8 hour chase, the polypeptide with an $M_r$ of 33,000 became almost undetectable in the protoplasts and was accompanied by a corresponding increase in the level of a polypeptide with an $M_r$ of 28,000. The level of unprocessed Cuc Chit-CTPP ($M_r$ 33,000) in the media increased slightly during the chase time course. These results imply that the Cuc Chit-CTPP proprotein ($M_r$ 33,000) was processed to a polypeptide with an $M_r$ of 28,000 and retained intracellularly. The rate of Cuc Chit and Cuc Chit-CTPP secretion and processing were quantitated by densitometric analysis of SDS-PAGE fluorogram (FIG. 10). At room temperature Cuc Chit was secreted from tobacco leaf protoplast with a half-life ($t_{1/2}$) of approximately 1.5 hours. Processing of the Cuc Chit-CTPP fusion protein occurred with a $t_{1/2}$ of 2.1 hours.

Subcellular Localization of Cuc Chit and Cuc Chit-CTPP Fusion Proteins

It has been previously shown that the 23-kD proprotein and the mature 18-kD subunit of BL are localized in the microsomal fraction and vacuoles of transgenic tobacco cells, respectively (Wilkins, T. A., et al., Plant Cell 2, 301–313 (1990)). The subcellular localization of Cuc Chit and Cuc Chit-CTPP were examined by organelle isolation as shown in FIG. 11 and by electron microscopic immunocytochemistry as shown in FIG. 12. Protoplasts for vacuole isolation were prepared from the same transgenic plants used in the pulse/chase experiments (FIG. 10) to insure similar levels of Cuc Chit and Cuc Chit-CTPP fusion protein expression and vacuoles were isolated as described in Methods. Activities of enzymes specific for the cytosol (glucose-6-phosphate dehydrogenase, EC 1.1.1.49)(Simcox, P. D., et al., L. Plant Physiol. 59, 1128–1132 (1977)), the ER (NADH cytochrome c reductase, EC 1.6.99.3) (Lord,, J. M., Endoplasmic reticulum and ribosomes. In Isolation of membranes and organelles from plant cells, J. L. Hall and A. L. Moore, eds (New York: Academic Press), pp. 119–134 (1983)), and the vacuole (α-mannosidase, EC 3.2.1.24) (Boller, T. and H. Kende, Plant Physiol. 63, 1123–1132 (1979)) were compared in crude protoplast and vacuole lysates. Vacuole fractions from Cuc Chit and Cuc Chit-CTPP plants contained 10% NADH cytochrome c reductase and ≦5% glucose-6-phosphate dehydrogenase, relative to total protoplast associated activity. The subcellular distribution of Cuc Chit and Cuc Chit-CTPP proteins was examined by immunoblot analysis of the protoplast and vacuole lysates using Cuc Chit polyclonal sera. Gels were loaded such that each lane contained the same amount of total vacuolar protein, with respect to α-mannosidase activity. The processed form of Cuc Chit-CTPP proprotein ($M_r$ 28,000) was detected only in the vacuole fraction from Cuc Chit-CTPP protoplasts, indicating that the CTPP is sufficient for redirection of Cuc Chit to the vacuoles of plants (FIG. 11, lane 4).

Localization of Cuc Chit in transgenic tobacco plants was also analyzed by electron microscopic immunocytochemistry. Thin sections of transgenic tobacco leaves expressing Cuc Chit and Cuc Chit-CTPP were treated with Cuc Chit antiserum. Antibody binding was visualized with 15-nm-diameter colloidal gold linked to protein A. Cuc Chit was localized in the cell wall and middle lamella of tobacco cells expressing Cuc Chit (FIG. 12A), whereas colloidal gold labeling was readily discernible in the vacuoles of tobacco cells expressing Cuc Chit-CTPP (FIG. 5C). A very low level of labeling was also detected in the cell wall of these cells. No specific labeling was detected in parallel experiments using non-immune sera as the primary antibody (FIG. 12B and 12D).

DISCUSSION:

Sorting of vacuolar and lysosomal proteins from other secretory proteins requires specific targeting information contained within the molecular structure of these polypeptides. Chimeric proteins containing a secreted protein and various regions of a vacuolar protein have been used to characterize vacuolar targeting information in yeast (Johnson, L. M., et al., Cell 48, 875–885 (1987); and Klionsky, D. J., et al., Mol. Cell. Biol. 8, 2105–2116 (1988)). Using a similar approach, it has been demonstrated that the vacuolar sorting determinant of the plant protein BL, is contained within a 15 amino acid CTPP. BL is initially synthesized as a glycosylated proprotein and is subsequently processed prior to or concomitant with deposition of the protein in the vacuole, by removal of the glycosylated CTPP. Similarly, both Cuc Chit-CTPP and Cuc Chit-proBL fusion proteins were initially synthesized as proproteins and processed to their mature form by the removal of the CTPP, intracellularly. It has been further demonstrated by organelle purification and electron microscopy immunocytochemical localization, that the $M_r$ 28,000 processed form of Cuc Chit-CTPP is localized in the vacuoles of tobacco cells expressing Cuc Chit-CTPP. Thus, the proBL CTPP was sufficient to redirect a secreted protein, cucumber chitinase, to the plant vacuole.

The role of the 18-kD subunit of BL was analyzed on the sorting of Cuc Chit-BL and Cuc Chit-proBL fusion proteins. The Cuc Chit-proBL fusion protein was processed by removal of the CTPP and the mature protein was retained intracellularly, whereas the Cuc Chit-BL fusion protein lacking the CTPP was efficiently secreted from the cell. Similarly, a mutant form of BL lacking the CTPP was secreted from transgenic tobacco protoplasts (Bednarek, S. Y., et al., Plant Cell 2, 1145–1155 (1990)). Together these results suggest that within the 18-kD subunit of BL there are no additional targeting elements sufficient for sorting of the protein to the vacuole.

Sorting Efficiency

Redirection of cucumber chitinase by the CTPP to the vacuole was not complete. It was found that 70 to 75% of total radiolabeled Cuc Chit was localized in the vacuole and the remaining Cuc Chit-CTPP proprotein was secreted into the incubation media. In contrast to the mixed distribution of Cuc Chit-CTPP, the Cuc Chit-proBL fusionprotein was efficiently retained intracellularly (95%, FIG. 9, lane 3). The additional 18-kD BL subunit may present the CTPP in a more favorable structural context for sorting. Insertion of a "random spacer" peptide preceding the CTPP in the Cuc Chit-CTPP fusion protein may, likewise, facilitate efficient vacuolar sorting.

Targeting element(s) within a fusion protein may not be presented in the proper secondary and/or tertiary structural context and result in the complete or partial secretion of chimeric protein. Johnson et al (Johnson, L. M., et al., Cell 48, 875–885 (1987)) determined that the first 30 amino acids of the yeast vacuolar CPY proprotein efficiently retained the secreted protein invertase, intracellularly, whereas a 10-amino acid region of the CPY propeptide was only effective at retaining 45% of the invertase fusion protein. Valls et al. (Valls, L. A., et al., J. Cell Biol. 111, 361–368 (1990)) suggest that fusion or deletions near this region containing the tetrapeptide QRPL, which is critical for CPY sorting, may interfere with the structural context in which the signal is presented and result in missorting of the CPY or the CPY-invertase fusion protein.

Analysis and Comparison of Plant Vacuolar Sorting Determinants

In addition to the Gramineae lectins, other soluble vacuolar proteins have been identified that are processed by removal of a carboxyl-terminal propeptide (see Chrispeels, M. J., Plant Mol. Biol. 42, 21–53 (1991) for review). Similar to BL, the carboxyl-terminal extension of the basic isoform of tobacco chitinase is also necessary for sorting and sufficient to redirect a cucumber chitinase fusion protein to the vacuole (Neuhaus and Boller, in press). The primary sequences of the proBL CTPP and the basic tobacco chitinase isoform carboxyl-terminal extension are not homologous.

The basic and acidic isoforms of β-1,3-glucanases and chitinases from tobacco have been shown to be localized intracellularly and extracellularly, respectively (see Chrispeels, M. J., Plant Mol. Biol. 42 21–53 (1991) for review). A comparison of the deduced amino acid sequences of the acidic and basic β-1,3-glucanase and chitinase isoforms reveals that the vacuolar isoforms contain additional carboxyl-terminal extensions not found on the extracellular isoforms (Linthorst, J. H. M., et al., Mol. Plant-Microbe. Interact. 3, 252–258 (1990); and Neale, A. D., et al., Plant Cell 2, 673–684 (1990)). Similar to BL, tobacco β-1,3-glucanase is initially synthesized as a glycosylated precursor and processed to the mature protein by removal of the glycosylated carboxyl-terminal propeptide (Shinshi, H., et al., Proc. Natl. Acad. Sci. U.S. 85, 5541–5545 (1988); Van den Bulcke, M., et al., Proc. Natl. Acad. Sci. U.S. 86, 2673–2677 (1989)); however, it remains to be determined whether the propeptide contains any sorting information.

In addition to carboxyl-terminal extensions, many plant and yeast vacuolar proteins are synthesized as precursors with an amino-terminal propeptide that is proteolytically removed just before or upon arrival in the vacuole. The amino-terminal propeptides of both CPY and the yeast vacuolar protein proteinase A contain elements sufficient for sorting to the vacuole (Johnson, L. M., et al., Cell 8, 875–885 (1987); Valls, L. A., et al., Cell 48, 887–897 (1987); Valls, L. A., et al., J. Cell Biol. 111, 361–368 (1990); and Klionsky, D. J., et al., Mol. Cell. Biol. 8, 2105–2116 (1988)). An amino-terminal propeptide from the sweet potato storage protein, sporamin, also contains a region necessary for vacuolar protein sorting in plants (Matsuoka, K., et al., Proc. Natl. Acad. Sci. U.S. 88, 834–838 (1991)). Deletion of this region led to secretion of the sporamin by transgenic tobacco cells, while prosporamin was processed and deposited within the vacuoles. However, to date, this region has not been demonstrated to be sufficient for sorting to the vacuole.

It is tempting to speculate that because a propeptide region is accessible to proteolytic processing, it would also present a sorting determinant in an accessible or favorable context. To date, no common consensus sequences or structural elements that function as vacuole localization signals in these amino and carboxyl-terminal propeptides have been identified. In addition, many plant vacuolar proteins are not synthesized as proproteins. Investigations into the mechanisms of sorting of PHA (Tague, B. W., et al., Plant Cell 2, 533–546 (1990) and the 11S globulin legumin (Saalbach, G., et al., Plant Cell 3, 695–708 (1991)) have found multiple regions of targeting information within these proteins. These results suggests there may be multiple independent mechanisms for vacuolar protein sorting.

Conclusions

It has been shown that deletion of the CTPP results in secretion of BL. These results indicate that the BL CTPP is both necessary and sufficient for vacuole protein sorting.

I claim:

1. A DNA encoding a sorting peptide which consists of a sequence selected from the group consisting of SEQ ID NOS: 7, 8 and 9.

2. The DNA of claim 1 which is SEQ ID NO: 7.

3. The DNA of claim 1 which is SEQ ID NO: 8.

4. The DNA of claim 1 which is SEQ ID NO: 9.

5. A DNA comprising a sequence selected from the group consisting of SEQ ID NO: 7, 8, and 9, wherein said sequence is fused to the 3' end of a coding sequence of a foreign protein having a N-terminal signal sequence which mediates translocation to the endoplasmic reticulum.

6. A DNA comprising a sequence encoding the sorting peptide SEQ ID NO: 6, wherein said sequence is fused to the 3' end of a coding sequence of a foreign protein having a N-terminal signal sequence which mediates translocation to the endoplasmic reticulum.

* * * * *

UNITED STATES PATENT AND TRADEMARK OFFICE

CERTIFICATE OF CORRECTION

PATENT NO. : 5,525,713

DATED : June 11, 1996

INVENTOR(S) : Natasha V. Raikhel

It is certified that error appears in the above-identified patent and that said Letters Patent is hereby corrected as shown below:

On the title page,

Column 1, after the Title, insert the following paragraph:

--Government Rights

This invention was funded under Department of Energy Contract No. DE-AC02-76ER01338. The U.S. Government has certain rights in this invention.--

Signed and Sealed this

Twenty-fifth Day of May, 1999

Attest:

Q. TODD DICKINSON

*Attesting Officer* *Acting Commissioner of Patents and Trademarks*